United States Patent
Wu et al.

(10) Patent No.: US 11,871,463 B2
(45) Date of Patent: *Jan. 9, 2024

(54) IMPLANTABLE MEDICAL DEVICE AND METHOD FOR MANAGING ADVERTISING AND SCANNING SCHEDULES

(71) Applicant: Pacesetter, Inc., Sylmar, CA (US)

(72) Inventors: Yongjian Wu, Saratoga, CA (US); Jyoti Bhayana, Milpitas, CA (US); Chao-Wen Young, Cupertino, CA (US); Tejpal Singh, Stevenson Ranch, CA (US); Samir Shah, Valencia (UA)

(73) Assignee: Pacesetter, Inc., Sylmar (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/972,728

(22) Filed: Oct. 25, 2022

(65) Prior Publication Data

US 2023/0039943 A1 Feb. 9, 2023

Related U.S. Application Data

(60) Continuation of application No. 16/838,719, filed on Apr. 2, 2020, now Pat. No. 11,516,860, which is a
(Continued)

(51) Int. Cl.
*H04W 76/14* (2018.01)
*H04W 4/23* (2018.01)
(Continued)

(52) U.S. Cl.
CPC ........ *H04W 76/14* (2018.02); *A61N 1/37223* (2013.01); *A61N 1/37252* (2013.01); *A61N 1/3956* (2013.01)

(58) Field of Classification Search
CPC ..... H04W 76/14; H04W 84/18; H04W 48/16; H04W 12/00; H04W 4/80;
(Continued)

(56) References Cited

U.S. PATENT DOCUMENTS 9,072,913 B2 7/2015 Jacobson
9,168,383 B2 10/2015 Jacobson et al.
(Continued)

*Primary Examiner* — Andrew Wendell
(74) *Attorney, Agent, or Firm* — Dean D. Small; The Small Patent Law Group, LLC

(57) ABSTRACT

A method and device for managing establishment of a communications link between an external instrument (EI) and an implantable medical device (IMD) are provided. The method stores, in a memory in at least one of the IMD or the EI, a base scanning schedule that defines a pattern for scanning windows over a scanning state. The method enters the scanning state during which a receiver scans for advertisement notices during the scanning windows. At least a portion of the scanning windows are grouped in a first segment of the scanning state. The method stores, in the memory, a scan reset pattern for restarting the scanning state. Further, the method automatically restarts the scanning state based on the scan reset pattern to form a pseudo-scanning schedule that differs from the base scanning schedule and establishes a communication session between the IMD and the EI.

19 Claims, 16 Drawing Sheets

Related U.S. Application Data division of application No. 15/707,862, filed on Sep. 18, 2017, now Pat. No. 10,639,482.

(60) Provisional application No. 62/396,655, filed on Sep. 19, 2016.

(51) Int. Cl.
*A61N 1/372* (2006.01)
*A61N 1/39* (2006.01)

(58) Field of Classification Search
CPC .............. H04W 12/00407; H04W 4/23; A61N 1/37223; A61N 1/37252; A61N 1/3956; H04B 1/3816; H04B 7/18565; H04B 7/18593
See application file for complete search history.

(56) References Cited

U.S. PATENT DOCUMENTS

| | | |
|---|---|---|
| 9,420,480 B2 | 8/2016 | Cili et al. |
| 9,949,660 B2 | 4/2018 | Weinberg et al. |
| 10,639,482 B2 | 5/2020 | Wu et al. |
| 11,516,860 B2 * | 11/2022 | Wu ..................... A61N 1/3956 |
| 2007/0061877 A1 | 3/2007 | Sima et al. |
| 2008/0228237 A1 | 9/2008 | Bange et al. |
| 2015/0148868 A1 | 5/2015 | Shahandeh et al. |
| 2018/0021589 A1 | 1/2018 | Wu et al. |
| 2018/0228237 A1 | 8/2018 | Zhang et al. |
| 2020/0015163 A1 | 1/2020 | Yang et al. |
| 2022/0223109 A1 | 7/2022 | Lai et al. |

* cited by examiner

IMPLANTABLE MEDICAL DEVICE AND METHOD FOR MANAGING ADVERTISING AND SCANNING SCHEDULES

CROSS REFERENCE TO RELATED APPLICATIONS

This application is a continuation application of U.S. patent application Ser. No. 16/838,719, filed Apr. 2, 2020, titled "IMPLANTABLE MEDICAL DEVICE AND METHOD FOR MANAGING ADVERTISING AND SCANNING SCHEDULES" which is a divisional application of U.S. patent application Ser. No. 15/707,862 filed Sep. 18, 2017, titled "IMPLANTABLE MEDICAL DEVICE AND METHOD FOR MANAGING ADVERTISING AND SCANNING SCHEDULES" (now U.S. Pat. No. 10,639,482, issued May 5, 2020), which claims the benefit of U.S. Provisional Application No. 62/396,655 filed Sep. 19, 2016, titled "IMPLANTABLE MEDICAL DEVICE AND METHOD FOR MANAGING ADVERTISING AND SCANNING SCHEDULES," the subject matter of which are incorporated by reference herein in their entirety.

BACKGROUND

Embodiments of the present disclosure generally relate to systems and methods for establishing a communication link between devices, and more particularly to managing advertising and scanning schedules utilized to establish communication links between implantable medical devices and external instruments.

An implantable medical device (IMD) is a medical device that is configured to be implanted within a patient anatomy and commonly employs one or more leads with electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing.

IMDs are programmed by, and exchange data with, external instruments controlled by physicians and/or the patient. The external instruments use commercial operating systems (e.g., iOS, Android) that communicate through wireless bi-directional communication links with the IMDs. The bi-direction communication link is formed based on advertisement notices received by the external instruments. The advertisement notices are broadcast by the IMD at a predetermined constant frequency based on the wireless protocol. However, the current drain expended by the IMD to broadcast the advertisement notices can be too high where battery life is a concern, particularly in smaller devices that have limited space for batteries. To conserve current drain, it has been proposed to transmit advertisement notices at a lower frequency than defined by the wireless protocol, such as by waiting several seconds or minutes between transmission of successive advertisement notices (e.g., instead of a few seconds or milliseconds).

However, many external instruments have built in constraints related to how long the external instrument will monitor for advertisement notices for usability and power consumption purposes. If an advertisement notice is not received by the external instrument within a predetermined number of monitoring periods, the external instrument may decrease the frequency of the monitoring period. If the external instrument misses an advertisement notice, minutes may pass before the external instrument begins to monitor for an advertisement notice. When multiple unsuccessful monitoring periods occur, the battery of the external instrument is undesirably drained.

Further, today many external instruments use Bluetooth low energy (BLE) to connect to an IMD. The external instrument (EI) may be configured to scan for IMD advertisements with a first duty cycle during a first portion of a scanning interval. For example, the EI may maintain scan windows 50%-60% of the time out of a few hundred milliseconds. When an IMD advertisement is not detected during a scan window within the first scanning interval, the EI continues to scan, but utilizes a slower duty cycle. For example, during a second scanning interval, the EI may maintain scan windows open only during 25%-30% out of the same period of a few hundred milliseconds. Accordingly, when a connection is not made early in the EI scanning process, an unduly long period of time may occur before an IMD advertisement overlaps with an EI scanning window.

In accordance with the foregoing, conventional BLE telemetry protocols causes an undue drain on the IMD battery. The drain occurs when the EI does not connect with the IMD during the first scanning interval (within scan Windows are opened more frequently). The IMD then has to advertise for a longer period of time. Currently, the usage of the EI BLE Application program interface (API) results in an inconsistent connectivity to the IMD even among devices utilizing the same operating system (OS). A need exists for improved methods and systems to manage a communication link between the external instrument and an IMD.

BRIEF SUMMARY

In accordance with embodiments herein, a method is provided for managing establishment of a communications link between an external instrument (EI) and an implantable medical device (IMD). The method comprises storing, in memory in at least one of the IMD or the EI, an advertising schedule that defines a pattern for advertisement notices. The advertisement notices are distributed un-evenly and separated by unequal advertisement intervals. The method transmits, from a transmitter in at least one of the IMD or the EI, the advertisement notices distributed as defined by the advertising schedule. The method includes determining, at the IMD, when a connection request is received from the EI in connection with one of the advertisement notices. The method establishes a communications session between the IMD and the EI.

Optionally, the advertising schedule may include first and second advertisement intervals associated with first and second advertisement notices, respectively. The first and second advertisement intervals may differ from one another. The transmitting operation may comprise transmitting the first and second advertisement notices based on the first and second advertisement intervals. The method may alternate the transmitting operation between the first and second advertisement intervals. The advertising schedule may include at least first, second and third advertisement notices. The first and second advertisement notices may be spaced apart by a first advertisement interval and the second and third advertisement notices may be spaced apart by a second advertisement interval that is longer than the first advertisement interval.

The method may change the advertising schedule by at least one of i) changing one or both of first and second advertisement intervals, or ii) adding a third advertisement interval, in order to update the pattern for the advertisement notices. The method may further repeat the transmitting operation, over an advertising state. When a connection request from the EI is not detected, the method may determine a duration of the advertising state and perform the changing operation when the duration of the advertising state exceeds a predetermined threshold. Additionally or alternatively, the method may detect a new EI, and may perform the changing operation when the EI changes from a first EI to a second EI.

In accordance with embodiments herein, a method is provided for managing establishment of a communications link between an external instrument (EI) and an implantable medical device (IMD). The method comprises storing, in memory of at least one of the IMD or the EI, a scanning schedule that defines a pattern for scanning windows over a scanning state, wherein the scanning windows are grouped in a first segment of the scanning state. The method includes scanning for advertisement notices, utilizing a receiver in at least one of the IMD or the EI, during scanning windows, wherein the scanning windows are grouped in the first segment as defined by the scanning schedule. The scanning operation is repeated and the method establishes a communication link between the IMD and the EI. The method reconfigures the scanning schedule by changing at least one of i) a number of the scanning windows, ii) a spacing between the scanning windows or iii) a duration of the first segment, in order to update the pattern for the scanning windows.

Optionally, the scanning schedule defines a second segment of the scanning state. The second segment of the scanning state represents a quiescent segment that is devoid of scanning windows, wherein a duration of the second segment is at least as long as a duration of the first segment. Optionally, the scanning operation comprises opening at least first, second and third scanning windows, in the first segment, with an un-even spacing therebetween such that the first and second scanning windows are separated by a first scanning interval and the second and third scanning windows are separated by a different second scanning interval. Optionally, the scanning windows in the first segment are spaced apart from one another by scanning intervals, the scanning intervals linearly increasing between successive scanning windows.

In accordance with embodiments herein, an implantable medical device (IMD) is provided. The device comprises memory storing an advertising schedule that defines a pattern for advertisement notices. The advertisement notices are distributed un-evenly and separated by unequal advertisement intervals. A transmitter is configured to transmit the advertisement notices distributed un-evenly and separated by the unequal advertisement intervals as defined by the advertising schedule. A processor is configured to establish a communications link between the IMD and an external instrument (EI).

Optionally, the advertising schedule may include first and second advertisement intervals associated with first and second advertisement notices, respectively. The first and second advertisement intervals may differ from one another. The transmitter may be configured to transmit the first and second advertisement notices based on the first and second advertisement intervals. The transmitter may be configured to alternate transmission between the first and second advertisement intervals. The advertising schedule may include at least first and second advertisement notices to be spaced apart by an interval that may be shorter than a duration of at least one of the first or second advertisement notices. The processor may be further configured to determine when a connection request is received from the EI in connection with one of the advertisement notices.

Optionally, the processor may be further configured to change the advertising schedule by at least one of i) changing one or both of first and second advertisement intervals, or ii) adding a third advertisement interval, in order to update the pattern for the advertisement notices. The transmitter may be configured to repeat the transmitting operation, over the scanning state, when a connection request from the EI is not detected, and the processor is configured to determine a duration of the scanning state and perform the change when the duration of the scanning state exceeds a predetermined threshold. The processor may be further configured to detect a new EI and perform the change when the EI changes from a first EI to a second EI.

Optionally, the EI may use an app that manages scan and connection requests to ensure a high probability of connection during the first available device advertising cycle. The app technique bypasses the limitation in the mobile Bluetooth API that only performs intensive scan and connection requests right after the user makes a request. The Bluetooth scan and connect requests may slow down or discontinue scanning until a connect failure is detected and returned to the API, allowing the mobile device to save power, but causing connection issues with the aforementioned IMD. The BLE API connection technique also decreases battery life for the IMD. The Bluetooth connection request from the EI app will start a timer, lasting for a predetermined length of time. If no connection is established within the time interval, the request is aborted and a new connection request begins, maintaining the intensive scan and connection requests, increasing the likelihood of a timely connection, and assisting in preserving battery life for the IMD, which would have to be removed for battery issues.

In accordance with embodiments herein, a method is provided for managing establishment of a communications link between an external instrument (EI) and an implantable medical device (IMD). The method stores, in a memory in at least one of the IMD or the EI, a base scanning schedule that defines a pattern for scanning windows over a scanning state. The method enters the scanning state during which a receiver scans for advertisement notices during the scanning windows. At least a portion of the scanning windows are grouped in a first segment of the scanning state. The method stores, in the memory, a scan reset pattern for restarting the scanning state. Further, the method automatically restarts the scanning state based on the scan reset pattern to form a pseudo-scanning schedule that differs from the base scanning schedule and establishes a communication session between the IMD and the EI.

Optionally, the scanning windows may occur in the first segment based on a first duty cycle. The scanning windows occur in the second segment based on a second duty cycle that may be lower than the first duty cycle. The scan reset pattern may define the pseudo-scanning schedule to have a pseudo-duty cycle that may be higher than at least the second duty cycle associated with the second segment. The scanning windows in a second segment of the scanning state may be spaced apart based on a second scanning interval that may be longer than a scanning interval between the scanning windows in the first segment of the scanning state.

Optionally, the scan reset pattern may define the pseudo-scanning schedule to have a scanning interval between the scanning windows that is shorter than the second scanning interval associated with the second segment. The scan reset pattern may define a pattern for scan start requests and scan end requests that may be configured to form the pseudo-scanning schedule with a number of the scanning windows that may be great than the number of scanning windows in the base scanning schedule. The base scanning schedule may correspond to a Bluetooth connection schedule. The scan reset pattern may form a pseudo-scanning schedule having a higher duty cycle than a duty cycle corresponding to the Bluetooth connection schedule. An EI may store an application in memory. The application may be configured to communicate with the IMD. The application may define the scan reset pattern.

In accordance with embodiments herein, a device is provided. The device comprises memory to store a base scanning schedule that defines a pattern for the scanning windows over a scanning state. A radio frequency (RF) circuit is configured to communicate with an implantable medical device (IMD). The RF circuit is configured to enter a scanning state to scan for advertisement notices in accordance with the base scanning schedule. The memory stores a scan reset pattern for restarting the scanning state. /a processor is configured to direct the RF circuit to automatically restart the scanning state based on the scan reset pattern to form a pseudo-scanning schedule that differs from the base scanning schedule. The processor is configured to establish a communication link with the IMD.

Optionally, the scanning windows may be unevenly distributed across the base scanning schedule with at least a portion of the scanning windows grouped in a first segment of the scanning state. The device may further comprise an application stored in the memory. The application may be configured to direct the processor to restart the scanning state based on the scan reset pattern, when no advertisement notice is detected during the scanning windows. The scan reset pattern may include a predetermined reset interval. The processor may be configured to direct the RF circuit to end the scanning state and start a new scanning state at the expiration of the predetermined reset interval. The processor may be configured to repeatedly end and restart successive new scanning states until the RF circuit detects an advertisement notice from the IMD during one of the scanning windows.

The base scanning schedule may represent a Bluetooth connection schedule within an operating system. The scan reset pattern may be configured to modify operation of the RF circuit to provide the pseudo-scanning schedule. Scanning windows occur in the first segment based on a first duty cycle and the scanning windows occur in the second segment based on a second duty cycle that may be lower than the first duty cycle. The scan reset pattern may define the pseudo-scanning schedule to have a pseudo-duty cycle that may be higher than the second duty cycle associated with the second segment. The scanning windows in a second segment of the scanning state may be spaced apart based on a second scanning interval that may be longer than a scanning interval between the scanning windows in the first segment of the scanning state.

Optionally, the scan reset pattern may define the pseudo-scanning schedule to have a scanning interval between the scanning windows that may be shorter than the second scanning interval associated with the second segment. The scan reset pattern may define a pattern for scan start requests and scan end separated by a predetermined reset interval to form the pseudo-scanning schedule. The base scanning schedule may correspond to a Bluetooth connection schedule. The scan reset pattern may form a pseudo-scanning schedule having a higher duty cycle than a duty cycle corresponding to the Bluetooth connection schedule.

In accordance with embodiments herein, a method is provided for managing establishment of a communications link between an external instrument (EI) and an implantable medical device (IMD). The method stores, in a memory in at least one of the IMD or the EI, a base scanning schedule that defines a pattern for scanning windows over a scanning state an IMD application to communicate with the IMD, and a scan reset pattern to form a pseudo-scanning schedule that differs from the base scanning schedule. The method enters the scanning state during which an RF circuit scans for an advertisement notice during the scanning windows and determines whether the IMD application is running in a foreground state or a background state. The method further manages the scanning window in accordance with the pseudo-scanning schedule or the base scanning schedule based on the determining operation and established a communication session between the IMD and the EI.

Optionally, the managing operation, when in the foreground state, manages the scanning window in accordance with the pseudo-scanning schedule and, when in the background state, manages the scanning window in accordance with the base scanning schedule. The method may further comprise identifying that a scan timer expires before the advertising notice is detected during one of the scanning windows, and, in response to the identifying operation, when in the background state, automatically restart the scan timer and continuing the scanning state according to the base scanning schedule.

Optionally, the method may identify that the scan timer may expires before the advertising notice is detected during one of the scanning windows, and, in response to the identifying operation, when in the foreground state, automatically restart the scan timer, cancel the scanning state and enter a new scanning state defined by the base scanning schedule. The cancelling and entering operations may comprise cancelling a first connection request to the RF circuit and sending a second connection request to the RF circuit. The scan timer may be started when entering the scanning state and the determining operation may be performed when the scan timer expires. The scan timer may be associated with a scan reset pattern that defines a pattern for scan start requests and scan end requests that are separated by a predetermined reset interval to form the pseudo-scanning schedule.

In accordance with embodiments herein a device is provided. The device comprises memory to store a base scanning schedule that defines a pattern for scanning windows over a scanning state and to store a scan reset pattern to form a pseudo-scanning schedule that differs from the base scanning schedule. A radio frequency (RF) circuit is configured to communicate with an implantable medical device (IMD). The RF circuit is configured to enter the scanning state to scan for advertisement notices in accordance with the base scanning schedule. One or more processors are configured to execute an IMD application to determine whether the IMD application is running in a foreground state or a background state, manage the scanning window in accordance with the pseudo-scanning schedule or the base scanning schedule based on the determine operation and establish a communication session with the IMD.

Optionally, when in the foreground state, the one or more processors may be configured to manage the scanning window in accordance with the pseudo-scanning schedule and, when in the background state, may manage the scanning window in accordance with the base scanning schedule. The one or more processors may be configured to identify that a scan timer expires before the advertising notice is detected during one of the scanning windows, and, in response to the identify operation, when in the background state, may automatically restart the scan timer and continue the scanning state according to the base scanning schedule.

Optionally, the one or more processors may be configured to identify that the scan timer expires before the advertising notice is detected during one of the scanning windows. In response to the identify operation, when in the foreground state, the processors may automatically restart the scan timer, cancel the scanning state and enter a new scanning state defined by the base scanning schedule. The cancelling and entering operations may comprise cancelling a first connection request to the RF circuit and sending a second connection request to the RF circuit. The scan timer may be started when entering the scanning state and the determine operation may be performed when the scan timer expires. The scan timer may be associated with a scan reset pattern that defines a pattern for scan start requests and scan end requests that are separated by a predetermined reset interval to form the pseudo-scanning schedule.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Various embodiments described herein include a method and/or system to manage advertisement and scanning schedules utilized in connection with establishing a wireless bi-directional communication link between an implantable medical device (IMD) and an external instrument (EI). The advertisement schedule is configurable to provide an uneven, unequal interval between successive advertisement notices. In accordance with at least one embodiment, an overall pattern for the advertisements may be managed to provide a total number of advertisement notices that is similar to existing even, constant intervals.

A technical effect of various embodiment described herein provides an advertising schedule that improves overall connectivity as compared to conventional advertising schedules. For example, the connectivity may be improved by shortening the time period that elapses while a user attempts to connect. Additionally or alternatively, a technical effect of various embodiments described herein provides a scanning schedule that improves overall connectivity as compared to conventional scanning schedules. The connectivity may also be improved by increasing the percentage of attempts that result in a connection, within a relatively short time period. By improving the connectivity, another technical effect of various embodiments described herein includes decreasing battery drain for both the IMD and the EI to establish a wireless bi-directional communication link.

Figure 1:
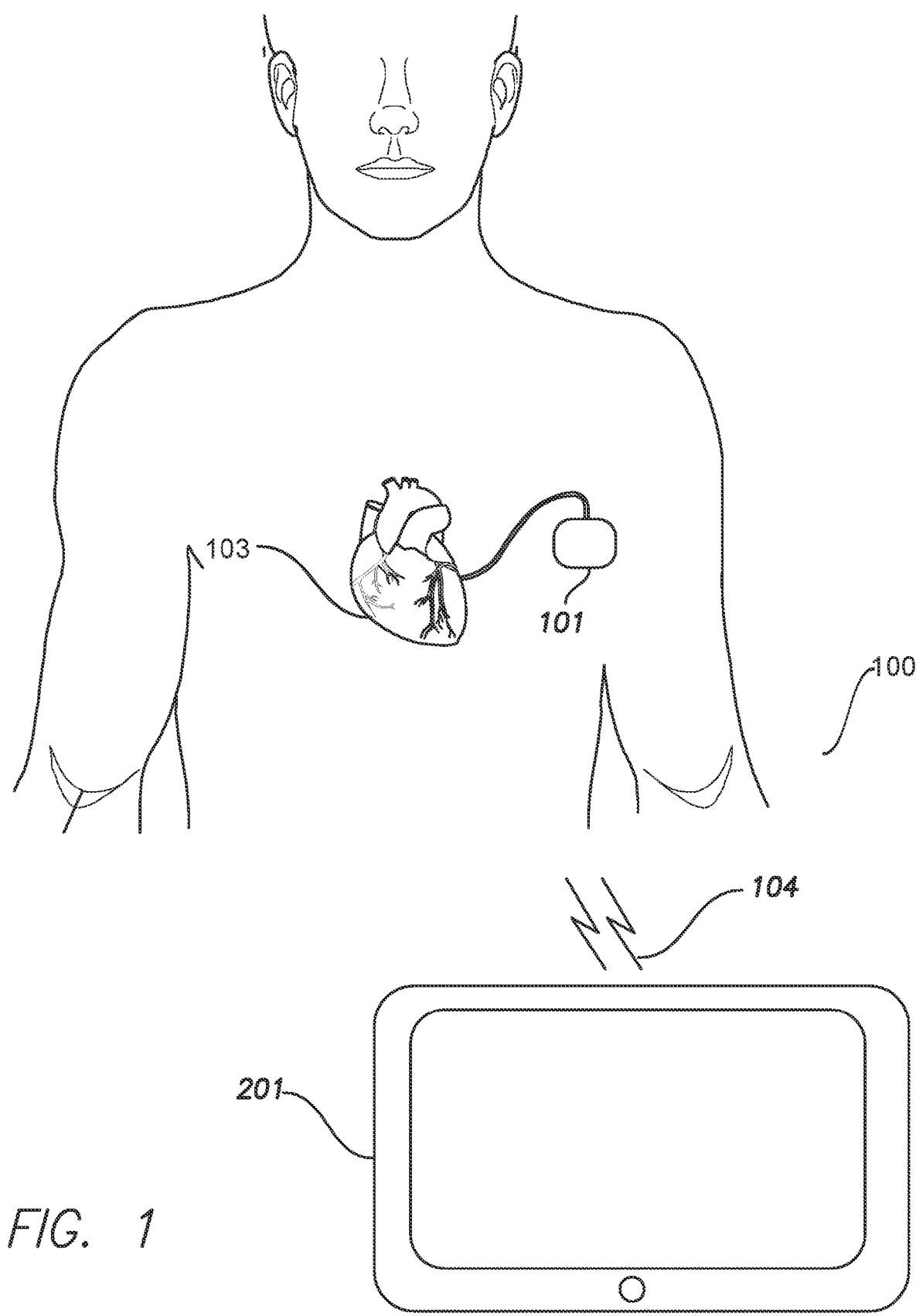
FIG. 1 illustrates simplified block diagram of a system for initiating a bi-directional communication link, according to an embodiment herein.

FIG. 1 illustrates a simplified block diagram of a system 100 for initiating a bi-directional communication link. The system 100 includes an IMD 101 and an EI 201 (e.g., table computer, smart phone, smart watch, laptop, and/or the like), according to an embodiment. The IMD 101 may be implanted within a patient (e.g., proximate to and/or within a heart 103, proximate to the spinal cord). Additionally or alternatively, the IMD 101 may have components that are external to the patient; for example, the IMD 101 may include an external pulse generator (EPG). Optionally, the IMD 101 may be one of various types of implantable devices, such as, for example, neurostimulator, patient, an implantable pacemaker, implantable cardioverter-defibrillator (ICD), defibrillator, cardiac rhythm management (CRM) device, an implantable pulse generator (IPG), or the like.

Optionally, the IMD 101 may be a leadless pacer, examples of which are disclosed in U.S. Pat. No. 9,072,913, entitled, "RATE RESPONSIVE LEADLESS CARDIAC PACEMAKER," and U.S. Pat. No. 9,168,383, entitled "LEADLESS CARDIAC PACEMAKER WITH CONDUCTED COMMUNICATION," which are expressly incorporated herein by reference. Additionally or alternatively, the IMD 101 may be a leadless monitor, examples of which are disclosed in U.S. patent application Ser. No. 15/084,373, filed Mar. 29, 2016, entitled "METHOD AND SYSTEM TO DISCRIMINATE RHYTHM PATTERNS IN CARDIAC ACTIVITY," which is expressly incorporated herein by reference.

The EI 201 is configured to establish a wireless bi-directional communication link 104 with the IMD 101. The communication link 104 allows the EI 201 to receive measurements from the IMD 101, and to program or send instructions to the IMD 101. The communication link 104 may use a standard wireless protocol such as Bluetooth Low Energy, Bluetooth, Medical Implant Communication Service, and/or the like. The EI 201 may be located within a home of the patient, a hospital, an automobile, at an office of the patient, or the like.

Figure 2:
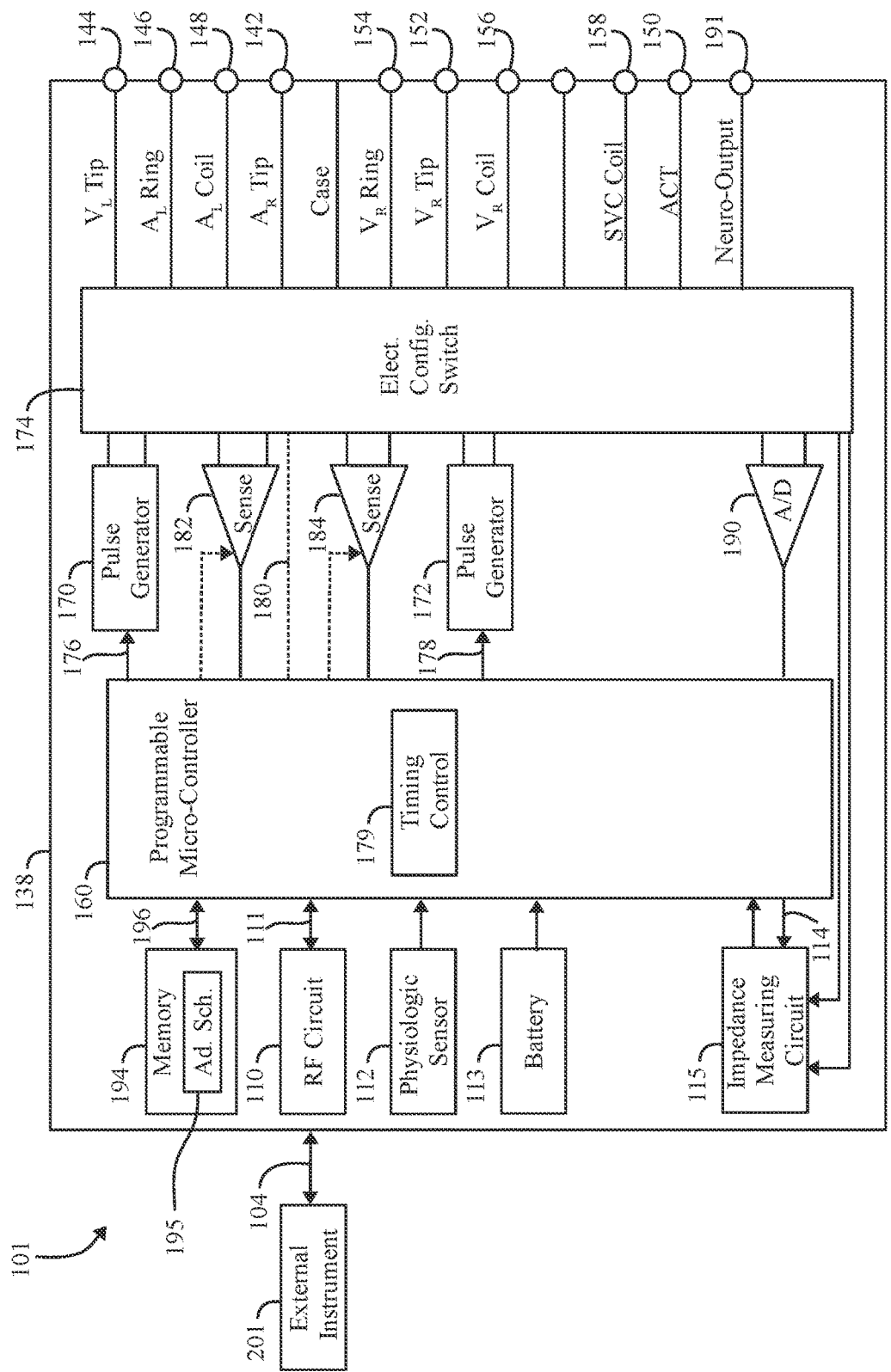
FIG. 2 illustrates a block diagram of an implantable medical device formed in accordance with embodiments herein.

FIG. 2 illustrates a block diagram of internal components of the IMD 101. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The IMD 101 is for illustration purposes only, and it is understood that the circuitry could be duplicated, eliminated or disabled in any desired combination to provide a device capable of treating the appropriate heart chamber(s) with cardioversion, defibrillation and/or pacing stimulation as well as providing for apnea detection and therapy. Additionally or alternatively, the IMD 101 may be used to generate neurostimulation for application to a desired area of a body, such as spinal cord stimulation, the brain and the like.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals. The terminals may be configured to be coupled to different types of electrodes and leads. FIG. 2 illustrates various non-limiting examples of types/positions of electrodes that may be utilized. All or a portion of the terminals may be used in various combinations. It is recognized that alternative types of electrodes may be utilized in place of, or in addition to, the examples of FIG. 2. The following examples are provided as non-limiting examples of terminals: 142 (right atrial tip electrode), 144 (left ventricular tip electrode), 146 (left atrial ring electrode), 148 (left atrial coil electrode), 150 (acoustical terminal, ACT electrode), 152 (ventricular tip electrode), 154 (right ventricular ring electrode), 156 (right ventricular coil electrode), and 158 (superior vena cava coil electrode). In addition, a terminal 191 is indicated to be representative of one or more neural stimulation electrodes that may be utilized in place of or in addition to the above noted electrodes.

The IMD 101 includes a controller circuit 160 which controls operation of the IMD 101. The controller circuit 160 (also referred to herein as a processor module or unit) may include one or more processors, or equivalent control circuitry, designed specifically for controlling the delivery of stimulation therapy and may further include RAM or ROM memory, logic and timing circuitry, state machine circuitry, and I/O circuitry. Typically, the controller circuit 160 includes the ability to process or monitor input signals (data) as controlled by program code stored in memory. The details of the design and operation of the controller circuit 160 are not critical to the invention. Rather, any suitable controller circuit 160 may be used that carries out the functions described herein. Among other things, the controller circuit 160 receives, processes, and manages storage of digitized cardiac data sets from the various sensors and electrodes. For example, the cardiac data sets may include IEGM data, pressure data, heart sound data, and the like.

The IMD 101 includes pulse generators 170, 172 to generate stimulation pulses for delivery by one or more leads and/or electrodes. The stimulation may be configured in different manners, such as in connection with neural stimulation, pacing pulse stimulation, cardioversion stimulation, defibrillation shocks, and the like The pulse generators, 170 and 172, may include dedicated, independent pulse generators, multiplexed pulse generators or shared pulse generators. The pulse generators, 170 and 172, are controlled by the controller circuit 160 via appropriate control signals, 176 and 178, respectively, to trigger or inhibit the stimulation pulses.

The pulse generators 170, 172 may be represent atrial and/or ventricular pulse generators, where the stimulation pulses are delivered through a plurality of electrodes and/or leads located within or proximate to the heart. Optionally, the pulse generators 170, 172 may represent neurostimulation pulse generators to generate stimulation pulses for a brain or spinal cord nervous system. The stimulation pulses are delivered by a plurality of electrodes through the neuro output lead 191. The neuro stimulation pulse generator circuit is controlled by the controller circuit 160 via appropriate control signals to trigger or generate the stimulation pulses.

The controller circuit 160 further includes timing control circuitry 179 used to control the timing of such stimulation pulses (e.g., the neural stimulation waveforms, pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the controller circuit 160, determines the polarity of the stimulation pulses (e.g., unipolar, bipolar, etc.) by selectively closing the appropriate combination of switches (not shown).

A sensing circuit 182 and sensing circuit 184 may also be selectively coupled to one or more leads through the switch 174 for collecting sensed physiologic data (e.g., cardiac activity, neural activity, respiratory activity, etc.). The sensing circuits, 182 and 184, may include dedicated sense amplifiers, multiplexed amplifiers or shared amplifiers. The outputs of the sensing circuits, 182 and 184, are connected to the controller circuit 160 which, in turn, receives the sensed data and is able to trigger or inhibit the pulse generators, 170 and 172, respectively, in a demand fashion in response to the absence or presence of activity of interest.

Sensed signals are also applied to the inputs of an analog-to-digital (ND) data acquisition system 190. The data acquisition system 190 is configured to acquire IEGM signals, neural signals, and the like. The data acquisition system 190 converts the raw analog data into a digital signal, and stores the digital signals in memory 194 for later processing and/or RF transmission to the EI 201. The data acquisition system 190 is coupled to one or more leads through the switch 174 to sample signals across any combination of desired electrodes. The data acquisition system 190 may also be coupled, through switch 174, to one or more of the acoustic sensors. The data acquisition system 190 acquires, performs ND conversion, produces and saves the digital pressure data, and/or acoustic data.

The RF circuit 110 may be configured to handle and/or manage the bi-directional communication link between the IMD 101 and the EI 201. As explained herein, the RF circuit 110 transmits, among other things, advertising notices in accordance with one or more advertising schedules 195. The RF circuit 110 also scans for connection requests from the EI 201. The RF circuit 110 is controlled by the controller circuit 160 and may support one or more wireless communication protocols while communicating with the EI 201, such as Bluetooth low energy, Bluetooth, Medical Implant Communication Service (MICS), and/or the like. The RF circuit 110 may include a transmitter, receiver, and/or a transceiver. Optionally, the RF circuit 110 may be electrically coupled to an antenna (not shown). Protocol firmware may be stored in memory 194, which is accessed by the controller circuit 160. The protocol firmware provides the wireless protocol syntax for the controller circuit 160 to assemble data packets, advertisement notices, connection requests, connection responses, establish communication links 104, and/or partition data received from the EI 201.

The controller circuit 160 is coupled to the memory 194 by a suitable data/address bus 196, wherein the programmable operating parameters used by the controller circuit 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the controller circuit 160 to analyze the cardiac signals and heart sounds identify characteristics of interest and derive values for predetermined statistical parameters. The memory 194 stores one or more advertising schedules 195. The advertising schedule 195 may be loaded in the memory 194 at the time of manufacture, at the time of activation, at the time of installation or throughout operation. For example, an EI 201 may download one or more advertising schedules 195 to be used in connection with the corresponding EI 201. For example, when an IMD 101 initially begins communicating with a particular EI 201, the EI 201 may download a corresponding advertising schedule. Additionally or alternatively, a common advertising schedule 195 may be used with multiple EI 201. As a further example, the IMD 101 may update the advertising schedule 195 throughout operation, such as based upon the success rate at which communications links are established, based delays when establishing communications links and the like.

The pacing and other operating parameters of the IMD 101 may be non-invasively programmed into the memory 194 through the RF circuit 110 in bi-directional wireless communication with the EI 201. The RF circuit 110 is controlled by the controller circuit 160 and receives data for transmission over a control line 111. The RF circuit 110 allows intra-cardiac electrograms, pressure data, acoustic data, Sv02 data, and status information relating to the operation of IMD 101 (as contained in the controller circuit 160 or memory 194) to be sent to the EI 201 through an established bi-directional communication link 104. The RF circuit 110 also allows the EI 201 to program new pacing parameters and advertising schedules for the IMD 101.

To establish the communication link 104 between the EI 201 and the IMD 101, the controller circuit 160 may instruct the RF circuit 110 to transmit one or more advertisement notices on one or more advertisement channels corresponding to an advertising schedule 195 stored in memory 194. The advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement interval based on an advertising schedule stored in the memory 194 until the communication link 104 is established with the EI 201.

The IMD 101 may also include a physiologic sensor 112, such as an accelerometer commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. Optionally, the IMD 101 may include an impedance measuring circuit 115 which is enabled by the controller circuit 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be will soon as the obtained.

Figure 3:
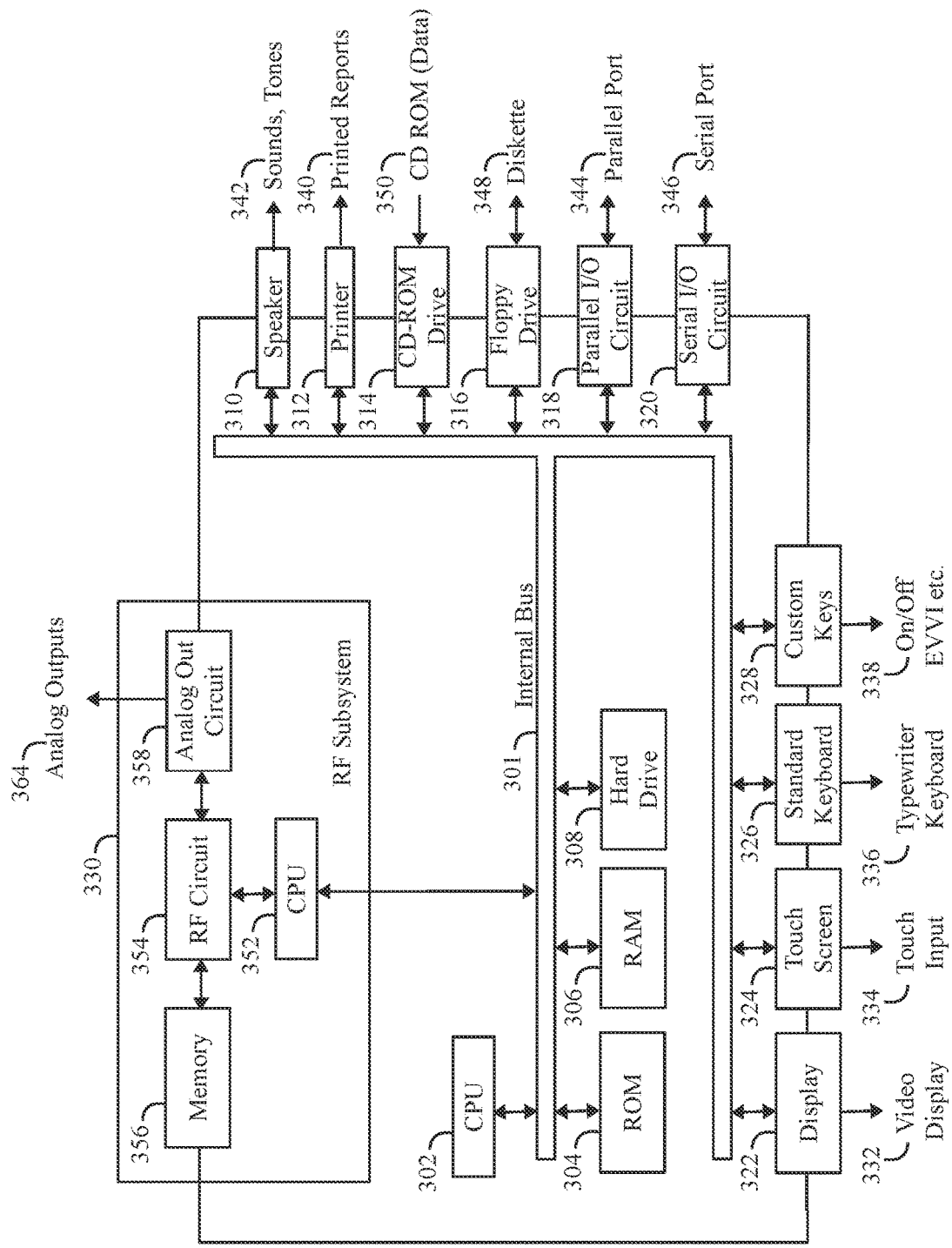
FIG. 3 illustrates a block diagram of an external instrument operated in accordance with embodiments herein.

FIG. 3 illustrates a functional block diagram of the EI 201 that is operated in accordance with embodiments herein. The EI 201 may be a workstation, a portable computer, a tablet computer, a smart watch, an IMD programmer, a PDA, a cell phone and/or the like. The EI 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the EI 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the EI 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the EI 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350. One or more scanning schedules are stored in the RAM 306, ROM 304, on a CD ROM 350, or elsewhere.

The RF subsystem 330 includes a central processing unit (CPU) 352 in electrical communication with an RF circuit 354, which may communicate with both the memory 356 and an analog out circuit 358. The analog out circuit 358 includes communication circuits to communicate with analog outputs 364. The EI 201 may wirelessly communicate with the IMD 101 and utilize protocols, such as Bluetooth, Bluetooth low energy, MICS, and/or the like. For example, the memory 356, ROM 304, and/or RAM 306 may include Protocol firmware, which is accessed by the CPU 352 and/or 302. The protocol firmware provides the wireless protocol syntax for the CPU 352 and/or 302 160 to assemble data packets, establish communication links 104, and/or partition data received from the IMD 101. The RF subsystem 330 and CPU 352 enter scanning states and establish communication sessions as described herein.

Advertisement and Scan Scheduling

Figure 4:
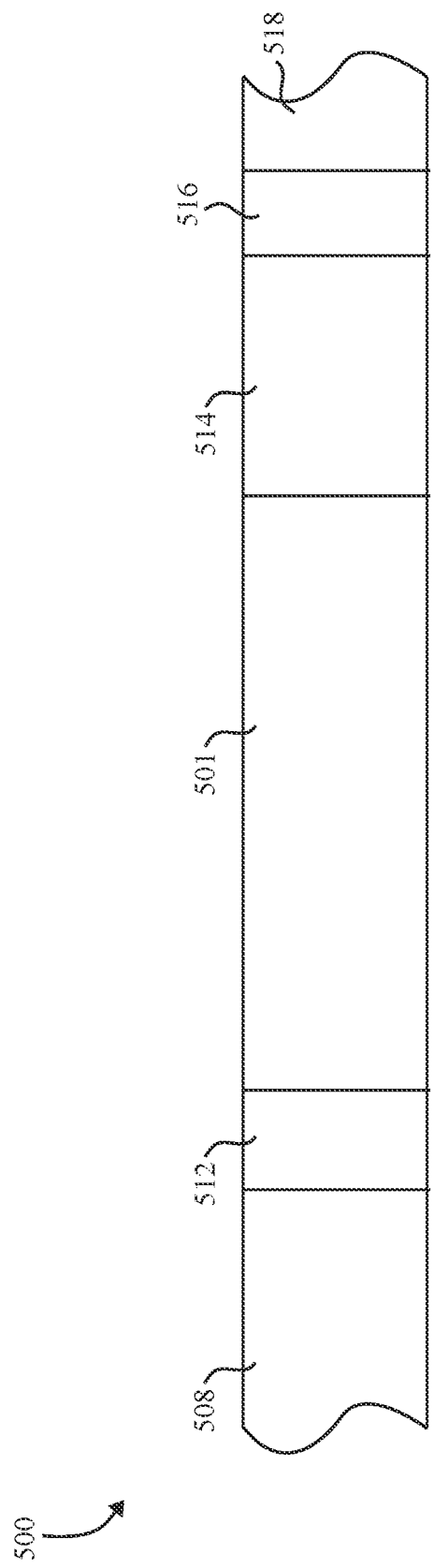
FIG. 4 is a timing diagram for establishing the wireless bi-directional communication link between the IMD and the EI in accordance with embodiments herein.

FIG. 4 is a timing diagram 500 for establishing the wireless bi-directional communication link 104 between the IMD 101 and the EI 201. The timing diagram 500 includes two communication sessions, a first communication session 501 and a second communication session 518. During the communication sessions 501, 518 the IMD 101 and the EI 201 may exchange data packets along the wireless bi-directional communication link 104. Each of the communication sessions 501, 518 are established by the IMD 101 and the EI 201 based on an advertising state 508, 514 defined as described herein. The advertising states 508, 514 are followed by an exchange of connection request and connection responses, which occurred during an interval generally referred to as an establishment state 512, 516.

During the advertising state 508 and 514, the IMD 101 may periodically transmit data packets corresponding to advertisement notices along one or more advertising channels. For example, the advertisement notices may be repeated, at intervals defined by an advertising schedule. The advertisement notices may include frequency synchronization information utilized to form the communication link 104, address information of the IMD 101, address information of the EI 201, pairing and/or bonding information, and/or the like to form the wireless bi-directional communication link 104. The information contained in the advertisement notice may be utilized by the EI 201 to establish the wireless bi-directional communication link.

During the scanning operations, the EI 201 scans for the advertisement notices and upon detection transmits a connection request to the IMD 101 to establish the wireless bi-directional communication link 104. The EI 201 monitors the one or more advertisement channels during a scanning window for the advertisement notice. The scanning window corresponds to a length of time the EI 201 may listen to the one or more advertising channels for the advertisement notice. When the EI 201 receives the advertisement notice, the EI 201 may transmit a data packet representing a connection request along the advertisement channel of the received advertisement notice to the IMD 101. The connection request may include instructions, such as a frequency of the data channel for the wireless bi-directional communication link 104. When the IMD 101 receives and confirms the connection request, the IMD 101 may monitor the data channel identified within the connection request for further instructions from the EI 201, thereby establishing the bi-directional communication link 104 starting the communication sessions 501, 518. Additionally or alternatively, the EI 201 and the IMD 101 may initiate a pairing and/or bonding procedure as described in in U.S. Patent Publication No. 2015/0148868, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

During the communication session 518, the IMD 101 may transmit sensed data concerning the patient. For example, the IMD 101 may transmit cardiac information, patient physiological information, pulsing information, and/or the like acquired by the IMD 101. The EI 201 may receive the sensed data from the IMD 101. Additionally or alternatively, the EI 201 may reconfigure the IMD 101. For example, the EI 201 may transmit new stimulation parameters, clear the sensed data store in the memory 194, and/or the like. The EI 201 and/or the IMD 101 may further terminate the communication session 518 closing the wireless bi-directional communication link 104 between the EI 201 and the IMD 101. When the link 104 is closed, the IMD 101 returns to a state in which the IMD 101 transmits advertisement notices in accordance with the advertising schedule.

Figure 5A:
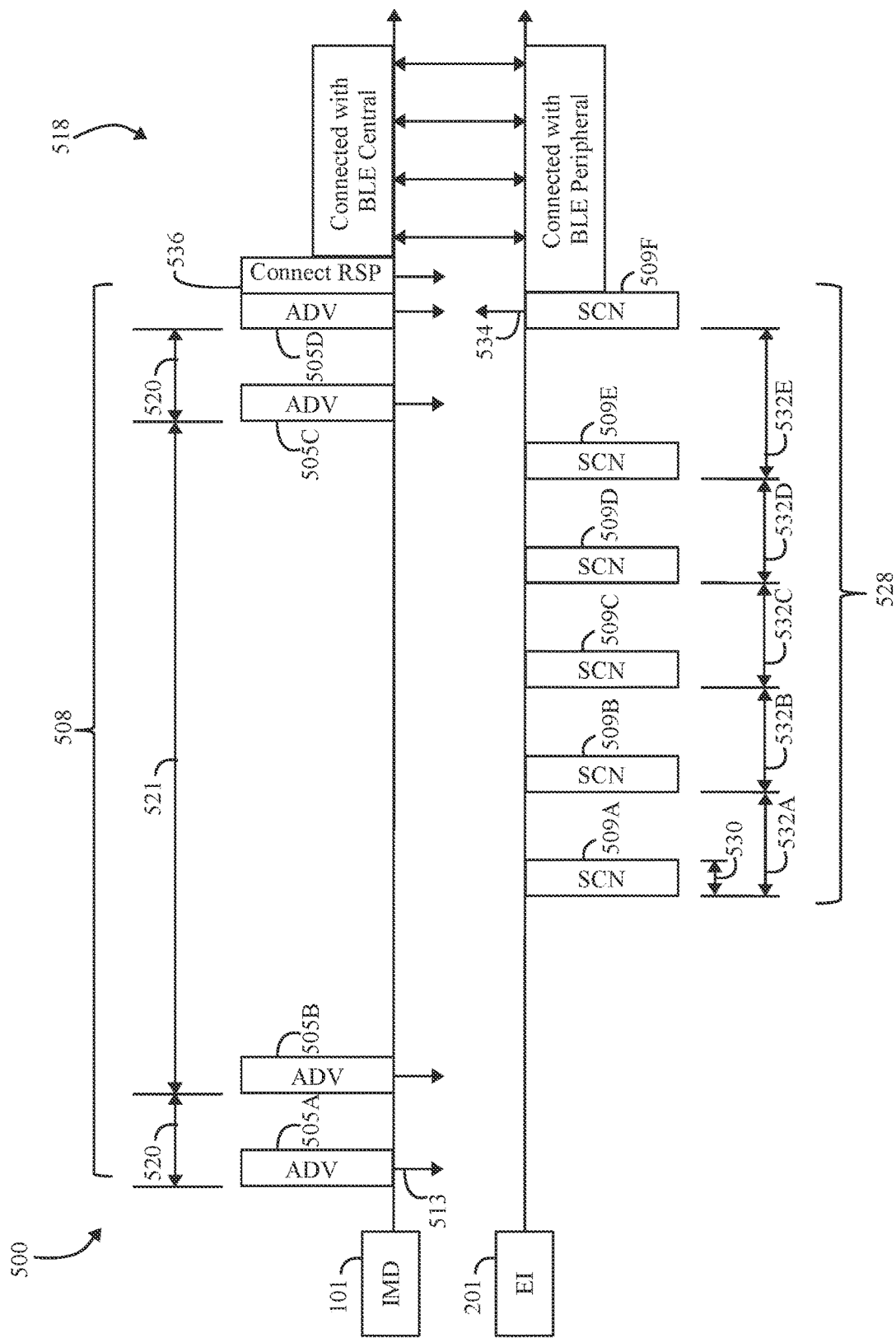
FIG. 5A illustrates an example of an advertising schedule and scanning schedule followed by the IMD and the EI, respectively, in accordance with embodiments herein.

FIG. 5A illustrates an example of an advertising schedule and scanning schedule followed by the IMD 101 and the EI 201, respectively, in connection with establishing the communications session 518. Prior to establishing the communications session 518, the IMD 101 and EI 201 performed transmitting and scanning operations independently of one another. The IMD 101 and EI 201 perform advertising and scanning operations asynchronously, with respect to one another. More specifically, the IMD 101 enters the advertising state 508, remains in the advertising state 508, and terminates the advertising state 508 in accordance with a predetermined protocol independent of and without knowledge of the scanning schedule or scanning state 528 of the EI 201. For example, the IMD 101 may transmit advertisement notices indefinitely, while in the advertising state 508. Alternatively, the IMD 101 may enter the advertising state 508 for predetermined periods of time, followed by quiescent periods of time in which no advertisement notices are transmitted.

Similarly, prior to establishing a communications session 518, the EI 201 enters, remains in, and terminates the scanning state 528 (repeatedly) in accordance with the scanning schedule independent, and without knowledge, of the advertising schedule or advertising state 508 of the IMD 101. For example, the EI 201 may remain in the scanning state 528 indefinitely, or for predetermined durations, followed by quiescent periods of time in which no scanning operations are performed. The IMD 101 remains in the scanning state 528 until the IMD 101 and EI 201 begin exchanging connection information. While the IMD 101 and EI 201 exchange connection information, the IMD 101 and EI 201 may be considered in the establishing state 512 (FIG. 4) to establish a communications session 518 therebetween.

During the advertising state 508, the IMD 101 transmits advertisement notices 505A-505D based on a predetermined advertising schedule (e.g., 195 in FIG. 2). The advertising schedule defines a pattern for the advertisement notices 505A-D, in which the advertisement notices 505A-D are distributed unevenly and separated by unequal advertisement intervals 520, 521. Each advertisement notice has a predetermined notice duration, during which the IMD 101 conveys advertisement information 513. The advertisement information 513 represents one or more data packets that may contain various information, such as frequency synchronization information utilized to form the bi-directional communication link 104 (FIG. 1), address information of the IMD 101, address information of the EI 201, and/or the like. The advertising information 513 may contain additional data and information as defined by the wireless protocol. Additionally or alternatively, the advertisement notices 505A-D may include pairing and/or bondable information (e.g., passkey seed information). The advertisement notices 505A-D are repeated based on the adverting schedule, until the wireless bi-directional communication link 104 is established.

The advertisement notices 505A-505D are separated from one another by advertisement intervals 520, 521 that extend from the beginning of one advertisement notice to the beginning of the next successive advertisement notice. As defined by the advertisement schedule, the first advertisement interval 520 is different in duration (e.g., shorter) than the duration of the second advertisement interval 521. For example, the advertisement interval 521 is substantially longer (e.g., several times longer) than the advertisement interval 520. The advertising schedule defines, among other things, the advertisement intervals 520, 521, an order in which different advertising intervals 520, 521 are to be applied, the advertisement information 513 and the like. The advertisement intervals 520, 521 may be defined in terms of a number of clock cycles based on an internal system clock of the IMD 101.

Turning to the EI 201, the EI remains in the scanning state 528 until the IMD 101 and EI 201 exchanging connection information. During the scanning state 528, the EI 201 scans for advertisement notices during a series of scanning windows 509A-509F based on a scanning schedule. The scanning schedule defines a pattern for the scanning windows 509A-509F, each of which has a predetermined scan duration 530. The scanning windows 509A-F are spaced apart by scanning intervals 532A-532E, where the scanning intervals 532A-532E represent the duration of time between the beginning of successive scanning windows (e.g., 509A and 509B). In the embodiment of FIG. 5A, the scanning intervals 532A-532E each differ in length, and increase in duration (relative to one another) over the course of the scanning state 528. For example, within the set of scanning intervals 532A-532E, the scanning interval 532A is the shortest interval, while the scanning interval 532E is the longest interval, and the scanning intervals 532B-532D have intermediate progressively longer durations.

In the example of FIG. 5A, scanning windows 509A-509F are distributed across a full length of the scanning state 528. Optionally, the scanning windows may be distributed over only a portion of the scanning state 528, while the remaining portion of the scanning state 528 is void of scanning windows. Further, in the example of FIG. 5A, the scanning intervals 532A-E are distributed in a linearly increasing manner over the scanning state 528, such that the scanning intervals 532A-532E are progressively longer in duration that the preceding scanning interval. Optionally, the scanning windows may be distributed in a different manner. For example, a portion of the scanning windows may be spaced apart by a first common scanning interval, while another portion of the scanning windows are spaced apart by a different second scanning interval, etc. In the example of FIG. 5A, the scanning windows 509A-509F have equal duration 530. Optionally, different scanning windows within the scanning state 528 may have different durations.

The IMD 101 and EI 201 operate asynchronously with respect to one another. In connection there with, the advertising state 508 begins and ends at times independent of, and not aligned with, a beginning and ending of the scanning state 528. As explained herein, the advertising schedule may be modified to increase a likelihood that advertisement notices will temporally aligned with scanning windows.

In the example of FIG. 5A, the advertisement notices 505A, 505B occur outside of the scanning state 528. Further, the advertisement notice 505C occurs within the scanning state 528, but between two consecutive scanning windows 509E and 509F. Advertisement notice 505D aligns with a scanning window 509F. During the scanning window 509F, the EI 201 detects the advertisement notice 505D. In response thereto, the EI 201 transmits a connection request 534 to the IMD 101. The IMD 101 receives the connection request 534 and in response thereto, returns a connection response 536 immediately thereafter. When the EI 201 detects the advertisement notice 505B, the IMD 101 and EI 201 enter the establishing state 512 (FIG. 4). The EI 201 returns the connection request 534, followed by the IMD 101 transmitting a connection response 536. Thereafter, the communication session 518 is established.

The content and format of the advertisement notices, connection requests and connection responses may vary based upon the wireless protocol being utilized by the EI 201 and IMD 101. For example, the EI 201 and the IMD 101 may utilize the Bluetooth Low Energy ("BLE") protocol. The BLE protocol is defined within "Bluetooth Specification Version 4.1," published Dec. 3, 2013 (incorporated herein by reference).

Figure 5B:
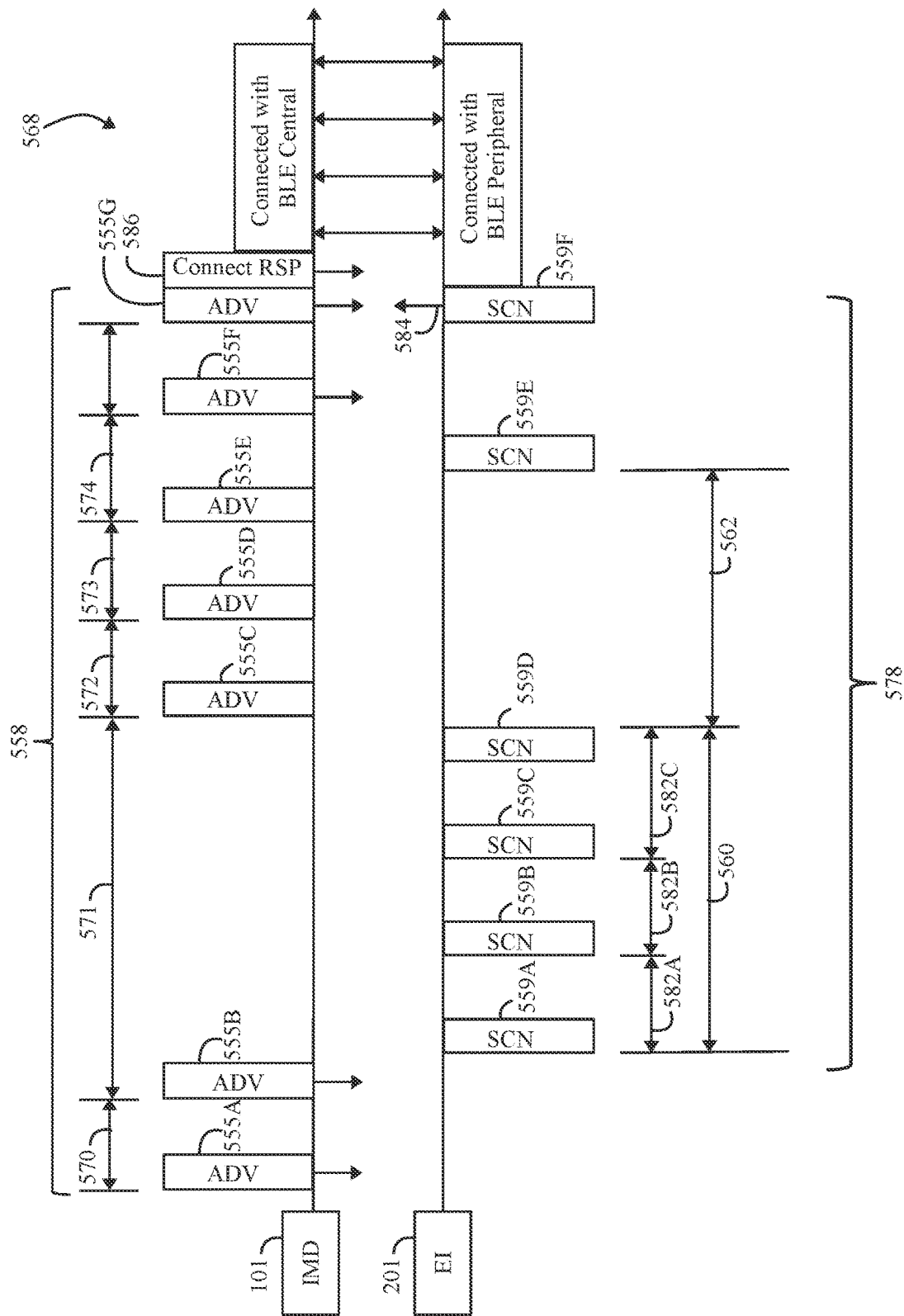
FIG. 5B illustrates a timing diagram for an advertising schedule and scanning schedule followed by the IMD and the EI, respectively, in accordance with an alternative embodiment.

FIG. 5B illustrates a timing diagram for an advertising schedule and scanning schedule performed by the IMD 101 and the EI 201 in accordance with an alternative embodiment. The IMD 101 remains in an advertising state 558 until exchanging connection information with the EI 201. During the advertising state 558, the IMD 101 transmits advertisement notices 555A-G in accordance with an advertising schedule. The advertisement notices 555A, 555B are separated by a first advertisement interval 570. Advertisement notices 555B-555C are separated by a second advertisement interval 571. Advertisement notices 555C-555F are separated by corresponding advertisement intervals 572-574. Each of advertisement intervals 570-574 differs in length, with the advertisement interval 570 being the shortest, the advertisement interval 571 being the longest, and advertisement intervals 572-574 having intermediate lengths.

The EI 201 perform scanning in accordance with a scanning schedule that defines a scanning state 578, within which scanning windows 559A-559F are grouped near one another within a first segment 560 within the scanning state 578. The scanning windows 559A and 559B are separated by a scanning interval 582A. The scanning windows 559B-559C are separated by scanning interval 582B. The scanning windows 559C-559D are separated by a scanning interval 582C. The scanning intervals 582A-582C differ in length and are progressively longer, with the first scanning interval 582A the shortest. The first segment 560 is followed by a quiet or quiescent (second) segment 562 that is devoid of any scanning windows.

In the example of FIG. 5B, the first segment 560 (including scanning windows) is located at the beginning of a scanning state 578. Optionally, the first segment 560 that includes scanning windows may be positioned at an end of the scanning state 578, or at any intermediate point therein. Additionally or alternatively, the scanning state 578 may include multiple segments, similar to segment 560 that include scanning windows. In addition, the scanning state 578 may include multiple quiescent segments 562 and/or position one or more of the quiescent segments 562 at the beginning, middle and/or in of the scanning state 578.

The advertising state 558 and scanning state 578 overlap in an asynchronous manner with none of the advertisement notices 555A-555F temporally overlapping a scanning window 559A-559D. However, during the next scanning state, the second scanning window 559F temporally aligns with an advertisement notice 555G. Accordingly, the EI 201 detects the advertisement notice 555G and returns a connection request 584. Thereafter, a connection response 586 is returned by the IMD 101 and a communication session 568 is established.

Figure 5C:
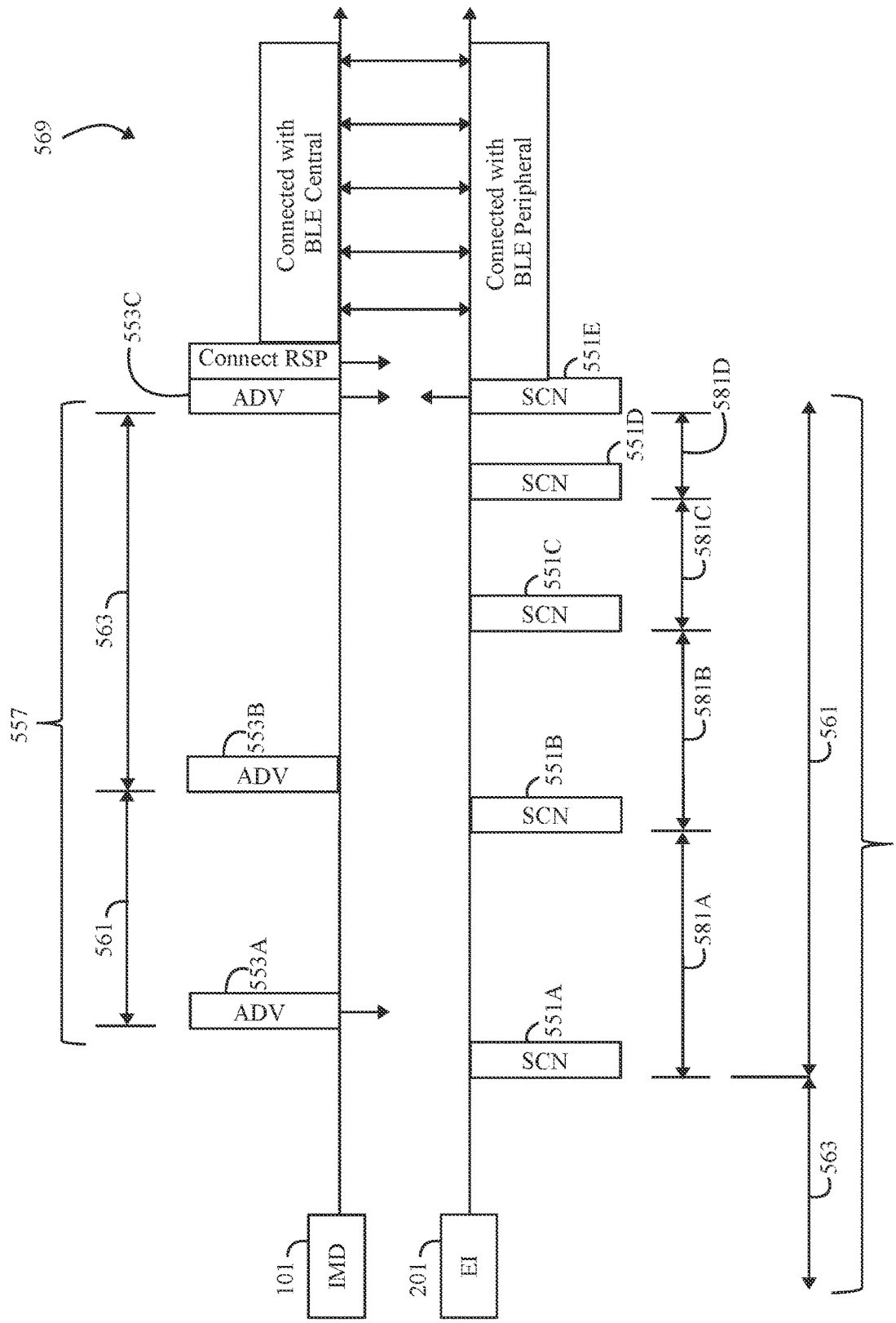
FIG. 5C illustrates a timing diagram for an advertising schedule and scanning schedule performed by the IMD and the EI in accordance with an alternative embodiment.

FIG. 5C illustrates a timing diagram for an advertising schedule and scanning schedule performed by the IMD 101 and the EI 201 in accordance with an alternative embodiment. The IMD 101 remains in an advertising state 557 and the EI remains in a scanning state 577 until exchanging connection information. During the advertising state 557, the IMD 101 transmits advertisement notices 553A-C in accordance with an advertising schedule. The advertisement notices 553A-553C are separated by first and second advertisement intervals 561, 563. The advertisement intervals 561-563 differ in length and become progressively longer, with the advertisement interval 561 being shorter than the next advertisement interval 563. Thereafter, the communication session 569 is established.

The EI 201 perform scanning in accordance with a scanning schedule that defines a scanning state 577, within which scanning windows 551A-551E are grouped in a segment 561 that follows an empty or quiescent segment 563 that lacks any scanning windows. The scanning windows 551A-551-E are separated by scanning intervals 581A-581D. The scanning intervals 581A-581D differ in length and are progressively shorter, with the first scanning interval 581A being longer than the next scanning interval 581B, which is longer than the next scanning interval 581C, etc.

In the embodiment of FIG. 5C the advertisement intervals 561-563 grow progressively longer, while the scanning intervals 581A-581D grow progressively shorter. The rates, at which the advertisement intervals and scanning intervals, change may be independent of one another, or may be a function of one another. For example, the advertisement intervals 561-563 may grow progressively longer at a rate that is dependent on, and a function of, the rate of change in the duration of the scanning intervals 581A-581D.

Figure 6A:
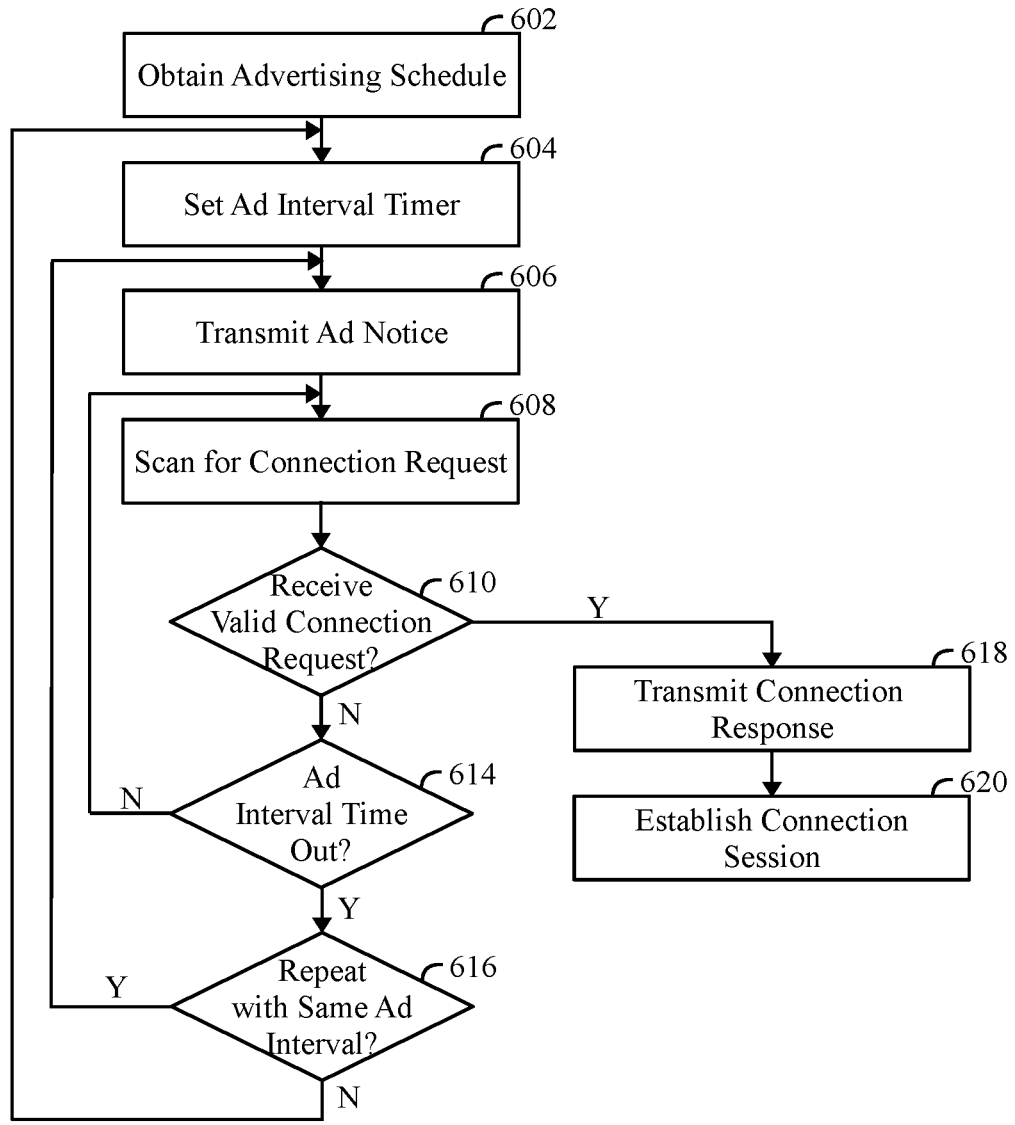
FIG. 6A illustrates a flowchart for a method performed by the IMD during the advertising state in accordance with embodiments herein.
Figure 6B:
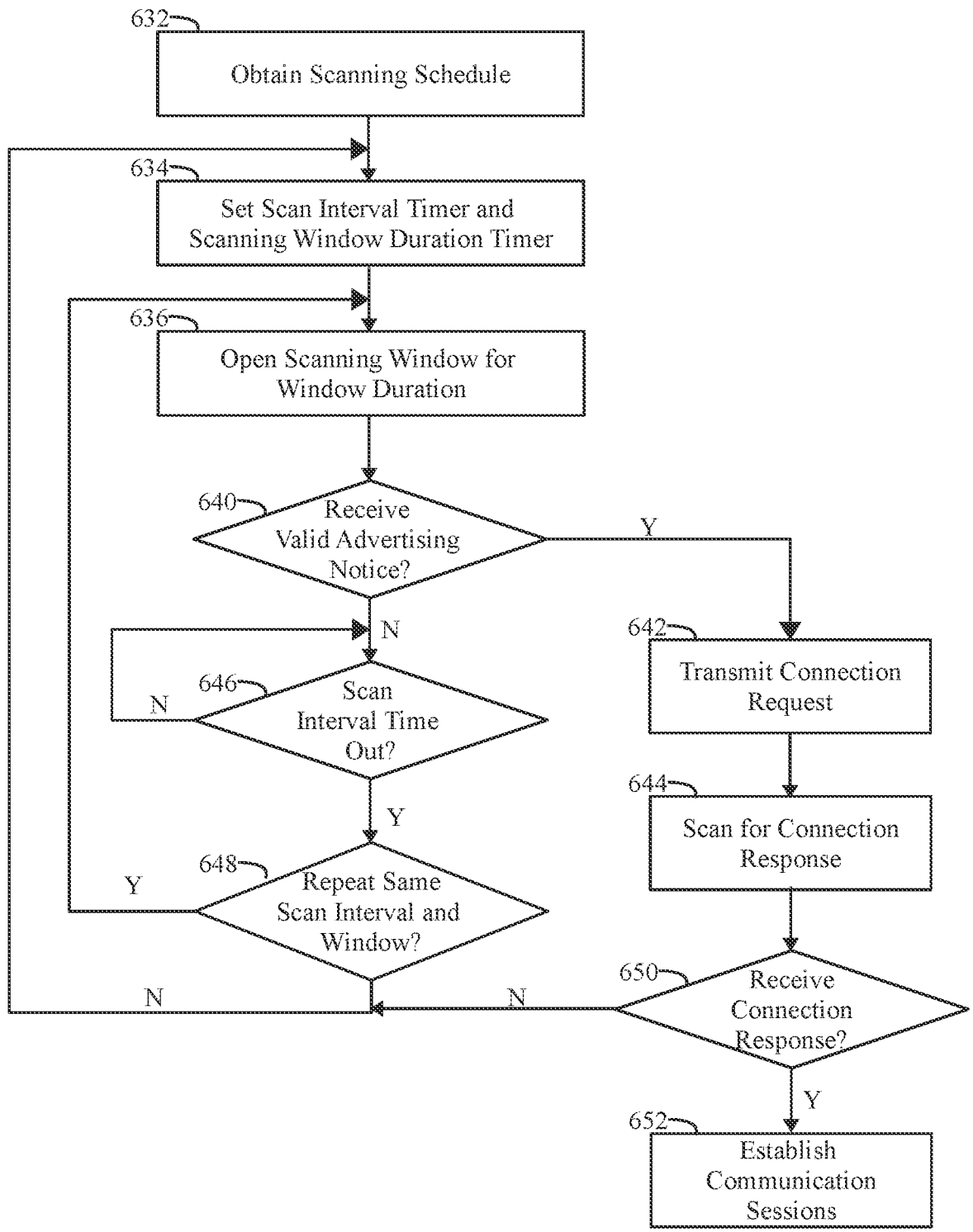
FIG. 6B illustrates a flowchart for a method performed by the EI during the scanning state in accordance with embodiments herein.

FIGS. 6A and 6B illustrate flowcharts of a method for managing advertising and scanning schedules utilized for establishing of a bi-directional communication link between the EI 201 and the IMD 101. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

FIG. 6A illustrates a flowchart for a method performed by the IMD 101 during the advertising state. At 602, the processor of the IMD 101 obtains an advertising schedule stored in memory. At 604, the processor sets an advertising interval timer to an advertising interval based on the advertising schedule. For example, with reference to FIG. 5A, the processor may set the advertising interval timer to correspond to the advertising interval 520.

At 606, the transmitter of the IMD 101 (e.g., RF circuit 110) transmits an advertisement notice. At 608, a receiver within the IMD 101 (e.g., RF circuit 110) scans one or more channels for a connection request. At 610, the processor of the IMD determines whether an incoming connection request is valid. For example, when a connection request is received, the content of the connection request is analyzed by the processor to determine whether the connection request is directed to the IMD 101 and has been transmitted from an authorized EI 201. For example, connection requests may be transmitted by various wireless devices. The IMD 101 may receive such connection requests even though various connection requests are not directed to the IMD 101, nor transmitted from an authorized EI 201. As one example, a valid connection request may include identification information corresponding to the IMD 101. For example, when the IMD 101 conveys an advertisement notice, the advertisement notice may include a serial number or other identification information unique to the IMD 101. An authorized EI 201, upon receiving an advertisement notice, returns the serial number and/or other identification information in a connection request. At 610, the IMD 101 analyzes the content of incoming connection request for the serial number and/or other identification information originally transmitted from the IMD 101 in advertisement notice.

Optionally, alternative information may be included in advertisement notice and connection request, and alternative types of analysis may be performed to validate incoming connection request, based on a corresponding protocol.

At 610, when a valid connection request is received, flow branches to 618. At 618, the advertising state is terminated and an establishing state is initiated in connection with establishing a communication session. At 618, the transmitter of the IMD 101 transmits a connection response. At 620, the IMD 101 and the EI 201 establish a communications session.

Alternatively, at 610, when no connection request is received or an invalid connection request is received, flow continues to 614. At 614, the processor of the IMD determined whether the advertising interval timer has timed out. At 614, when the interval timer times out, flow continues to 616. Otherwise, flow returns to 608, where the receiver continues to scan for a connection request. At 616, the processor of the IMD determines whether to repeat another advertising operation using the same advertising interval. When the same advertising interval is to be repeated for the next advertisement notice, flow returns to 606. Otherwise, flow returns to 604 where a new advertising interval is set from the advertising schedule.

For example, with reference to FIG. 5A, during a first iteration through the operations of FIG. 6A, the advertising interval timer is set to the advertising interval 520. During the second iteration, the advertising interval timer is set to a longer advertising interval 521. During a third iteration, the advertising interval is again set to the shorter advertising interval 520. Once advertising interval 505D is transmitted, a connection request 534 is received and flow branches in FIG. 6A as discussed above.

FIG. 6B illustrates a flowchart for a method performed by the EI 201 during the scanning state. At 632, the processor of the EI 201 obtains a scanning schedule stored in memory. At 634, the processor sets a scanning interval timer to a scanning interval based on the scanning schedule. For example, with reference to FIG. 5A, the processor may set the scanning interval timer to correspond to the scanning interval 532A. At 634, the processor also sets a window duration timer that defines the duration for the scanning window.

At 636, the receiver of the EI 201 opens a scanning window to scan for an advertisement notice. The receiver scans one or more channels for an advertisement notice. At 640, the processor of the EI 201 determines whether an advertisement notice was detected and if so, whether the incoming advertisement notice is from the IMD 101. For example, when an advertisement notice is received, the content of the advertisement notice is analyzed by the processor to determine whether the advertisement notice is directed to the EI 201 and has been transmitted from an authorized IMD 101. Advertisement notices are transmitted by various wireless devices. The EI 201 may detect advertisement notices from various devices, even though the advertisement notices are not directed to the EI 201, nor transmitted from the IMD 101. As one example, a valid advertisement notice may include identification information corresponding to the IMD 101. For example, when the IMD 101 conveys an advertisement notice, the advertisement notice may include a serial number or other identification information unique to the IMD 101. When a valid advertisement notice is detected, flow branches to 642. Otherwise flow continues to 646.

At 642, upon receiving a valid advertisement notice, the EI 201 returns a connection request. For example, the connection request may include an EI serial number and/or other EI identification information. The connection request may also include information from the advertisement notice. At 644, the EI 201 scans for a connection response. As explained above in connection with FIG. 6A, when the IMD 101 detects a valid connection request, the IMD 101 returns a connection response.

At 650, the processor determines whether a connection response has been received. When a connection response is received, flow moves to 652 where a communication session is established. Alternatively, when no connection response is received, at 650 flow branches to continue the scanning operations. In the example of FIG. 6B, when no connection response is received, the process may return to 634 where a new scanning interval timer and scanning window duration timer are set. Alternatively, flow may return to various other points within the operations of FIG. 6B. At 642, the scanning state is terminated and the establishing state is initiated in connection with establishing a communication session.

Alternatively, at 640, when no advertisement notice is received or an invalid advertisement notice is received, flow continues to 646. At 646, the processor of the EI 201 waits for the scanning interval timer to time out. At 646, when the interval timer times out, flow continues to 648. At 648, the processor of the EI 201 determines whether to repeat another scanning operation using the same scanning interval. When the same scanning interval is to be repeated for the next scanning window, flow returns to 636. Otherwise, flow returns to 634 where a new scanning interval is set.

For example, with reference to FIG. 5A, during a first iteration through the operations of FIG. 6B, the scanning interval timer is set to the scanning interval 532A and the window duration is set to window duration 530. During the second iteration, the scanning interval timer is set to a longer scanning interval 532B. During a third iteration, the scanning interval is again set to an even longer scanning interval 532C.

Figure 7:
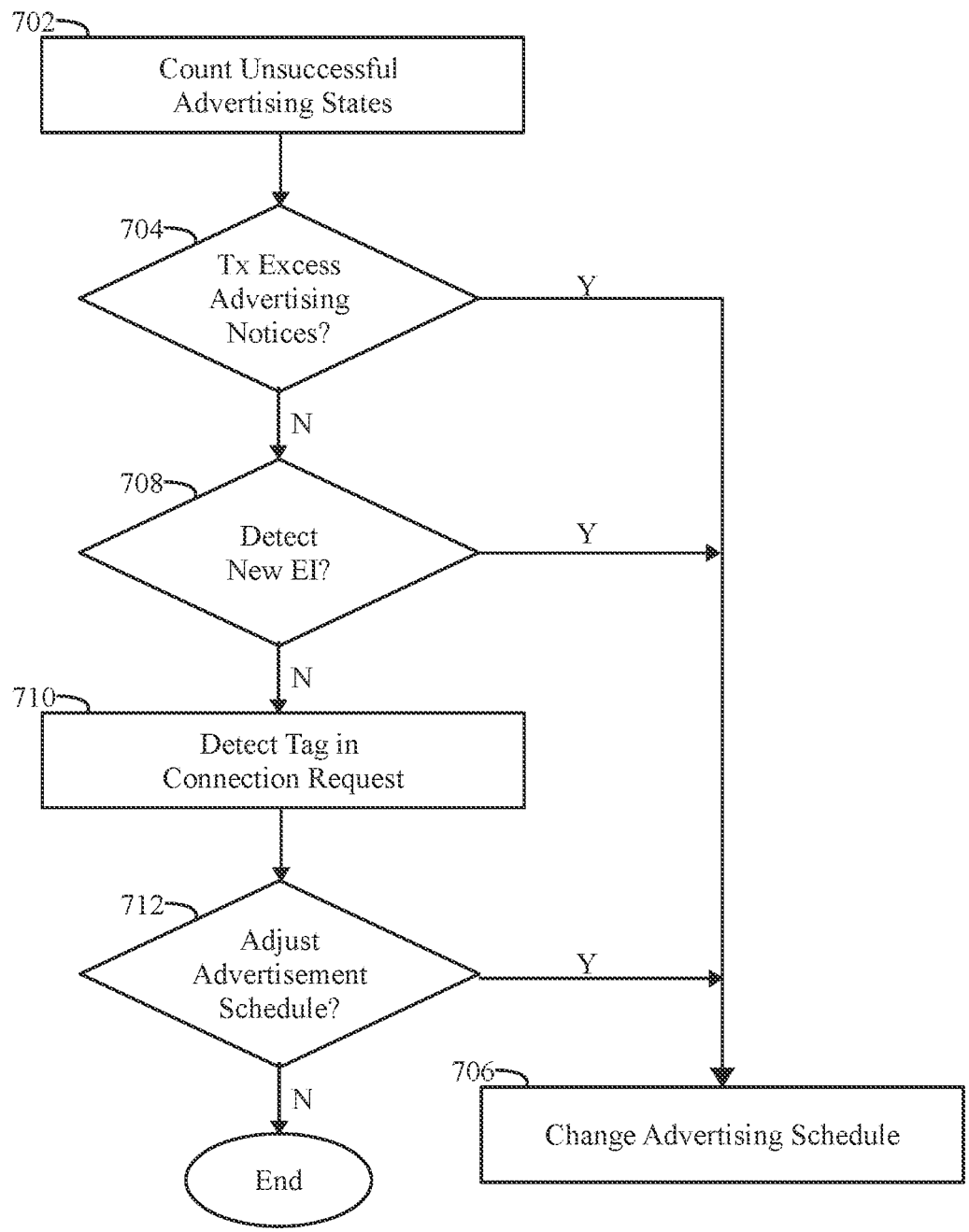
FIG. 7 illustrates a process for changing the advertisement schedule in accordance with an embodiment.

FIG. 7 illustrates a process for changing the advertisement schedule in accordance with an embodiment.

At 702, the processor of the IMD tracks the number of advertising states that have occurred without a successful connection. At 704, the processor of the IMD 101 determines whether the IMD 101 has transmitted an unduly large number of advertisement notices over an excessive number of advertising states without connecting with an EI 201. As explained herein, the transmitter of the IMD 101 repeats the transmitting operation over one or more advertising states, when a connection request from the EI is not detected. When the number of unsuccessful advertising states exceeds a predetermined threshold, flow moves to 706. At 706, the processor of the IMD 101 changes the advertising schedule. For example, the advertising schedule may be switched between predetermined advertising schedules. Additionally or alternatively, one or more advertisement intervals within the advertising schedule may be adjusted. For example, the advertising schedule may be changed by at least one of i) changing one or both of first and second advertisement intervals, or ii) adding a third advertisement interval, in order to update the pattern for the advertisement notices. For example, the advertising schedule may change from the schedule illustrated in connection with FIG. 5A to FIG. 5B, or from the schedule illustrated in connection with FIG. 5B to FIG. 5C, or otherwise.

At 708, the processor of the IMD 101, detects when a new EI is communicating with the IMD 101. When a new EI is detected, flow moves to 706 the processor of the IMD 101 may change from a first advertising schedule associated with a first EI, to a second advertising schedule associated with a second EI. It should be recognized that either advertising schedule may be useful with various different EI, however, different advertising schedules may be tailored to correspond to the scanning schedules associated with individual EI. Accordingly, the processor of the IMD 101 may change the advertising schedule based upon different EI that are communicating there with. For example, the IMD 101 may be configured to communicate with multiple EI. Each EI may have a different scanning schedule, power requirements and the like.

Additionally or alternatively, the operations at 710-712 may be performed, through which the IMD 101 learns a relation between the alignment of a scanning state and advertising state. At 710, the processor of the IMD 101 identifies a tag in a connection request (transmitted from an EI 201). The tag indicates the position of the scanning window (along the scanning state) at which the EI 201 first detected an advertisement notice. For example, when an EI 201 detects an advertisement notice during the first scanning window within a scanning state, the EI 201 may return (in the connection request) a tag indicating that the corresponding scanning window was the first scanning window in the scanning state. Alternatively, when the EI 201 detects an advertisement notice during a later scanning window or the last scanning window in the scanning state, the EI 201 returns a corresponding tag in the connection request. Based upon the tag within the connection request, at 710, the processor of the IMD 201 determines the point along the scanning state at which an advertisement notice was first detected.

At 712, the processor of the IMD determines whether to adjust the advertisement schedule based on the tag. For example, when the tag indicates that an early scanning window in a scanning state to detected an advertisement notice, no adjustment of the advertising schedule may be warranted. Alternatively, when the tag in a connection request indicates that a later or intermediate scanning window was the first scanning window to detect the advertising notice, and adjustment of the advertising schedule may be warranted. For example, the advertising schedule could be adjusted by shifting the advertising intervals, changing a number of scanning windows, shifting the positions of the scanning windows within the scanning state, or otherwise. The nature of the adjustment in the advertising schedule may be dependent on the position of the scanning window that detected the advertisement notice. When an adjustment in the advertisement schedule is warranted, flow moves to 706 where the advertising schedule is changed. Otherwise, the operations of FIG. 7 end.

Optionally, the method of FIG. 7 may be repeated to change the scanning schedule in one or more manners. For example, the scanning schedule may be changed by at least one of i) changing one or more scanning intervals, or ii) adding additional scanning intervals, in order to update the pattern for the scanning windows. For example, the scanning schedule may change from the schedule illustrated in connection with FIG. 5A to FIG. 5B, or from the schedule illustrated in connection with FIG. 5B to FIG. 5C, or otherwise. The scanning schedule may be changed for various reasons.

For example, the scanning schedule may be changed when the EI 201 scans for an unduly large number of scanning windows without connecting with an IMD 101. In connection there with, the receiver of the EI 201 repeats the scanning operation, over one or more scanning states, when an advertisement notice from the IMD is not detected. Periodically, the processor of the EI 201 determines a duration of one or more scanning states that have occurred without a successful connection. When the duration of the unsuccessful scanning states exceeds a predetermined threshold, the processor may change the scanning schedule. For example, the scanning schedule may be switched between predetermined scanning schedules. Additionally or alternatively, one or more scanning intervals within the scanning schedule may be adjusted.

Additionally or alternatively, the processor of the EI 201 may change the scanning schedule based upon different IMD that are communicating there with. For example, the EI 201 may be configured to communicate with multiple IMDs. Each IMD may have a different advertising schedule, power requirements and the like. The processor of the EI 201, may determine that the EI 201 is to communicate with a new IMD. In connection there with, the processor of the EI 201 may change from a first scanning schedule associated with a first IMD, to a second scanning schedule associated with a second IMD. It should be recognized that either scanning schedule may be useful with various different IMD, however, different scanning schedules may be tailored to correspond to the advertising schedules associated with individual IMD.

Next, embodiments are described to form a pseudo-scanning schedule followed by an EI, where the pseudo-scanning schedule differs from a base scanning schedule that is defined by firmware that is embedded within the operating system (OS) or the RF circuit of the EI.

Figure 8:
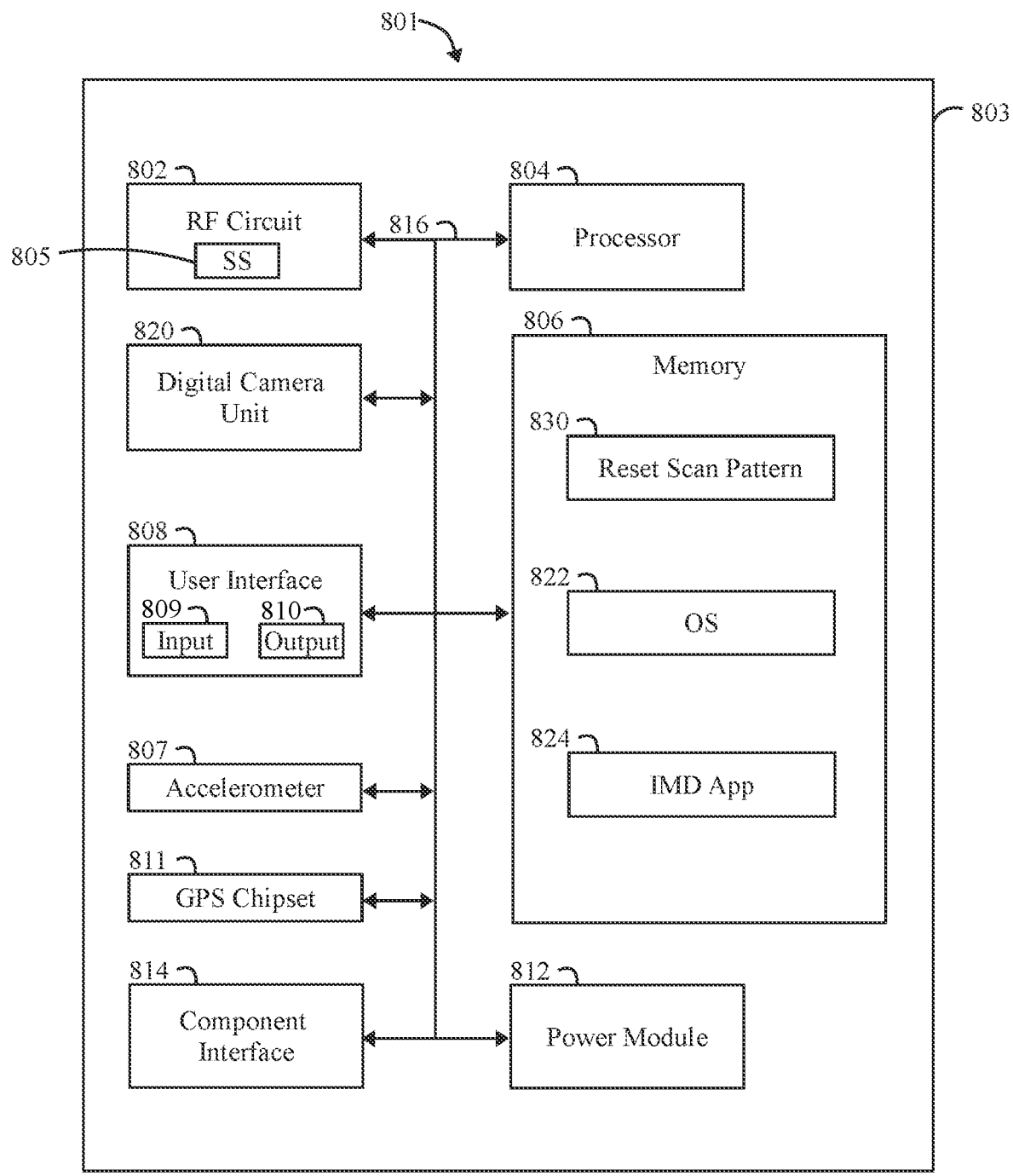
FIG. 8 illustrates a simplified block diagram of an EI formed in accordance with embodiments herein.

FIG. 8 illustrates a simplified block diagram of an EI 801 formed in accordance with embodiments herein. The EI 801 includes one or more wireless RF circuits 802, and one or more processors 804 (e.g., a microprocessor, microcomputer, application-specific integrated circuit, etc.). The EI 801 also includes one or more local storage medium (also referred to as a memory) 806, a GPS chipset 811, an accelerometer 807, a power module 812, a digital camera unit 820, and a component interface 814. The EI 801 also includes a user interface 808 that includes one or more input devices 809 and one or more output devices 810. The components of the EI 801 are operatively coupled to one another, and may be in communication with one another, by way of one or more internal communication links 816, such as an internal bus.

A housing 803 holds the processor(s) 804, memory 806, user interface 808, the digital camera unit 820 and other components. The input and output devices 809, 810 may each include a variety of visual, audio, and/or mechanical devices. For example, the input devices 809 can include a visual input device such as an optical sensor or camera, an audio input device such as a microphone, and a mechanical input device such as a keyboard, keypad, selection hard and/or soft buttons, switch, touchpad, touch screen, icons on a touch screen, a touch sensitive areas on a touch sensitive screen and/or any combination thereof. Among other things, the microphone may be utilized to record spoken requests from the user. Similarly, the output devices 810 can include a visual output device such as a liquid crystal display screen, one or more light emitting diode indicators, an audio output device such as a speaker, alarm and/or buzzer, and a mechanical output device such as a vibrating mechanism. Among other things, the speaker may be used to state instructions, ask questions and otherwise interact with the user. The display may be touch sensitive to various types of touch and gestures. As further examples, the output device(s) 810 may include a touch sensitive screen, a non-touch sensitive screen, a text-only display, a smart phone display, an audio output (e.g., a speaker or headphone jack), and/or any combination thereof. The user interface 808 permits the user to select one or more of a switch, button or icon in connection with normal operation of the EI 801.

The power module 812 preferably includes a power supply, such as a battery, for providing power to the other components while enabling the EI 801 to be portable, as well as circuitry providing for the battery to be recharged. The component interface 814 provides a direct connection to other devices, auxiliary components, or accessories for additional or enhanced functionality, and in particular, can include a USB port for linking to a user device with a USB cable. The GPS chipset 811 obtains GPS location information concerning the present position of the device. The accelerometer 807 detects movement and orientation of the EI 801.

The RF circuit 802 may utilize a known wireless technology for communication. The RF circuit 802 may represent one or more transmitters, one or more receivers and/or one or more transceivers that execute firmware in accordance with a corresponding communications protocol. The RF circuit 802 may include one or more local processors as part of, or in addition to, the transmitters, receivers, or transceivers. The RF circuit 802 executes firmware that includes, among other things, a scan schedule 805 that defines the durations of the scanning windows, scanning intervals, distribution of the scanning windows throughout a scanning state, duty cycle and the like.

The RF circuit 802 is controlled by the processor 804 and may support one or more wireless communication protocols while communicating with the INMD, such as Bluetooth low energy, Bluetooth, Medical Implant Communication Service (MICS), and/or the like. Optionally, the RF circuit 802 may be electrically coupled to an antenna (not shown). Optionally, protocol firmware may be stored in memory 806, which is accessed by the processor 804. The protocol firmware provides the wireless protocol syntax for the processor 804 to assemble data packets, advertisement notices, connection requests, connection responses, establish communication links, and/or partition data received from the IMD.

The memory (local storage medium) 806 may encompass one or more memory devices of any of a variety of forms (e.g., read only memory, random access memory, static random access memory, dynamic random access memory, etc.) and can be used by the processor 804 to store and retrieve data. The data that is stored by the memory 806 can include, but need not be limited to, operating systems, applications and informational data. The operating system includes executable code that controls basic functions of the communication device, such as interaction among the various components, communication with external devices via the wireless RF circuits 802 and/or the component interface 814, and storage and retrieval of applications and data to and from the memory 806. Each application includes executable code that utilizes an operating system to provide more specific functionality for the communication devices, such as file system service and handling of protected and unprotected data stored in the memory 806.

Applications stored in the memory 806 include various application program interfaces (APIs). Additionally, the applications stored in the memory 806 include an implantable medical device (IMD) application 824 that facilitates communication with the IMD, conveying program settings, updates, data and other information to the IMD. The IMD application 824 also receives patient related information, device related information and the like from the IMD. The ICM application 824 includes program instructions to direct the processor 804 to implement the methods, processes and operations described herein, and illustrated and described in connection with the FIGS.

In accordance with at least some embodiments, the RF circuit 802 stores (in local memory) the scanning schedule 805. The scanning schedule 805 represents a "base" scanning schedule that defines a pattern for the scanning windows over a continuous scanning state. The RF circuit 802 is configured to enter the scanning state, in response to a start scan request from the processor 804. The RF circuit 802 maintains the scanning state, during which scanning windows are opened and closed by the RF circuit 802 in accordance with the base scanning schedule 805. As explained herein, the distribution of the scanning windows may be varied according to different scanning schedules. For example, the scanning windows may be unevenly distributed across the base scanning schedule with at least a portion of the scanning windows grouped in a first segment of the scanning state. As one example, the base scanning schedule 805 may represent a Bluetooth connection schedule that is stored within firmware on the RF circuit 802 and/or within the operating system 822.

The memory 806 also stores a scan reset pattern 830 for repeatedly restarting the scanning state. The processor 804, under the control of the IMD application 824, directs the RF circuit 802 to restart automatically the scanning state based on the scan reset pattern 830 in order to form a pseudo-scanning schedule that differs from the base scanning schedule 805. The IMD application 824 is configured to direct the processor 804 to restart the scanning state when no advertisement notice is detected during the scanning windows within a predetermined period of time. For example, the scan reset pattern 830 may include a predetermined reset interval (e.g., a few milliseconds), where the IMD application 824 directs the processor 804 to end a current scanning state and start a new scanning state each time the predetermined reset interval expires. When no advertisement notices are detected, the processor 804 repeatedly ends and restarts successive new scanning states (e.g., with a frequency defined by the predetermined reset interval) until the RF circuit 802 detects an advertisement notice from the IMD during one of the scanning windows.

The scan reset pattern 830 modifies the operation (defined by the base scanning pattern 805) of the RF circuit 802 in order to provide a pseudo-scanning schedule which has a higher duty cycle than the base scanning pattern.

For example, the base scanning schedule may provide for scanning windows to occur in a first segment of the scanning state with a relatively high first duty cycle (e.g., 70-80%). The base scanning schedule may further provide for scanning windows to occur in a second segment of the scanning state with a lower second duty cycle (e.g., 30-40%) that differs from the first duty cycle. The scan reset pattern 830 may define the pseudo-scanning schedule to have a pseudo-duty cycle that is higher than the second duty cycle corresponding to the second segment of the scanning state for the base scanning schedule.

Optionally, the difference between the base scanning schedule and pseudo-scanning schedule may be defined in terms of the spacing between successive scanning windows. For example, the base scanning schedule may define the scanning windows in a second segment of the scanning state to be spaced apart based on a second scanning interval that is longer than a scanning interval between the scanning windows in the first segment of the scanning state. Accordingly, the scan reset pattern may define the pseudo-scanning schedule to have a scanning interval between the scanning windows that is shorter than the second scanning interval associated with the second segment. For example, the scan reset pattern defines a pattern for scan start requests and scan end requests that is configured to form the pseudo-scanning schedule with a number of the scanning windows that is great than the number of scanning windows in the base scanning schedule.

Figure 9:
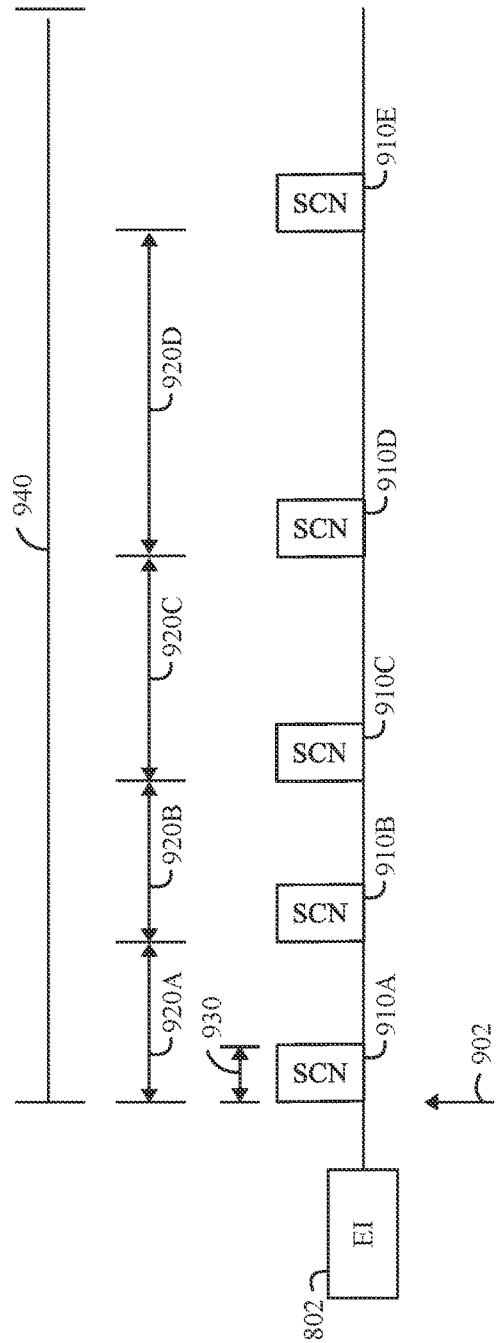
FIG. 9 illustrates a base scanning schedule defined within the firmware of an operating system and/or RF circuit of an EI in accordance with an embodiment herein.

FIG. 9 illustrates a base scanning schedule defined within the firmware of an operating system and/or RF circuit of an EI in accordance with an embodiment herein. The base scanning schedule is utilized by an EI to scan for, and connect to, an IMD, where the scanning schedule controls the scanning process and the EI operating system (OS) controls the connection process. For example, the EI may utilize a BLE connection process defined by firmware imbedded within the OS or an RF circuit. The BLE connection process includes, among other things, a scanning schedule that defines the duty cycle for the scanning windows. As explained herein, the scanning schedule defines the duration of the scanning windows and the scanning intervals between the beginnings of successive scanning windows.

The term duty cycle is used to refer to an amount/percentage of time over some time period of interest in which scanning windows are active and/or advertisement notices are being transmitted. For example, a scanning duty cycle of 50% would indicated that scanning windows are active (e.g., a receiver is "listening") for half of the time within a corresponding time period of interest (e.g., a scanning state). It is recognized that the scanning windows may not be evenly distributed over the time period of interest (e.g., scanning state). Instead, the scanning windows may be spaced more closely, with shorter scanning intervals there between, within a first segment of the of the scanning state. In the latter portion of the scanning state, the scanning windows may be spaced further apart with longer scanning intervals there between.

In the example of FIG. 9, the scanning schedule defines a pattern for the scanning windows 910A-910E, each of which has a predetermined scan duration 930. The scanning windows 910A-910E are spaced apart by scanning intervals 920A-920D. The intervals 920A-920D represent the duration of time between the beginning of successive scanning windows. In the embodiment of FIG. 9, the scanning intervals 920A-920D each differ in length and increase in duration relative to each previous interval over the course of the scanning state 940. For example, within the scanning state 940, the scanning interval 920A is the shortest interval. Scanning interval 920B is slightly longer, with 920C being longer, and 920D being the longest of the illustrated scanning intervals. Optionally, the scanning windows may be spaced in alternative manners, such as described in connection with FIGS. 5A-5C, or otherwise.

In accordance with some embodiments, the RF circuit 802 enters the scanning state 940 when receiving a scan start request 902. The RF circuit 802 remains in the scanning state 940, or for predetermined durations, followed by quiescent periods of time in which no scanning operations are performed. The RF circuit 802 may end a scanning state 940 based on various criteria. For example, the RF circuit 802 may determine that a "timeout" condition has occurred and end the scanning state 940. Additionally or alternatively, the RF circuit 802 may receive an instruction from the processor 804 to end a scanning state 940. The instruction may be based on various factors.

The details of the scanning schedules utilized by a BLE or other wireless protocol are stored within the firmware within the OS or RF circuit, and may not be available to application developers. For example, it may be assumed that, the developer of the IMD application is not familiar with the details of the base scanning schedule utilized by the EI. Hence, the IMD application developer is unaware of whether the base scanning schedule groups scanning windows 910A-E close to one another, far from one another or clustered in groups during different segments of the scanning state 940. The application developer is not aware of how the base scanning schedule spaces scanning windows over the scanning state (e.g., when no advertising notice is detected).

In accordance with embodiments herein, the IMD application 824 manages start scan requests and end scan requests to form a pseudo-scan schedule that exhibits a relatively high duty cycle for scanning windows as compared to a duty cycle of the case scanning schedule.

Figure 10:
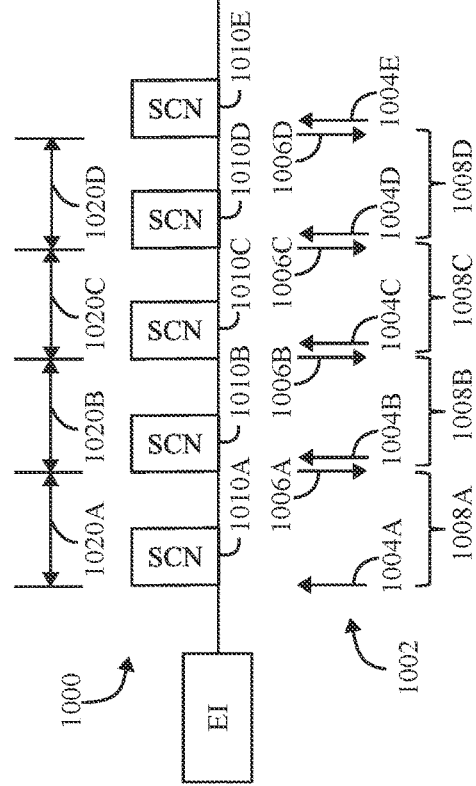
FIG. 10 illustrates a pseudo-scanning schedules utilized in accordance with embodiments herein.

FIG. 10 illustrates a pseudo-scanning schedule 1000 utilized in accordance with embodiments herein. The pseudo-scanning schedule 1000 is formed from a scan reset pattern 1002 (e.g., pattern 830 in FIG. 8). The scan reset pattern 1002 defines the pseudo-scanning schedule 1000 to have a pseudo-duty cycle that is substantially higher than a duty cycle associated with a base scanning schedule (e.g., FIG. 9). The scan reset pattern 1002 is defined by a series of scan start requests 1004A-E and scan end requests 1006A-D which are designated by arrows directed upward and downward, respectively. The successive scan start and scan end requests 1004A-E, 1006A-D are separated by predetermined reset intervals 1008A-D.

During operation, the IMD application 824 delivers a scan start request 1004A, and in response thereto, the RF circuit 802 enters a scanning state and opens a corresponding scanning window 1010A. The IMD application 824 waits for the predetermined reset interval 1008A and then conveys a scan end request 1006A, thereby causing the RF circuit 802 to end the scanning state. Immediately thereafter, the IMD application 824 conveys a new scan start request 1004B, and in response thereto, the RF circuit 824 begins a new scanning state and opens a corresponding scanning window 10106. The IMD application 824 waits for the predetermined reset interval 1008B and then conveys a scan end request 1006B, thereby causing the RF circuit 802 to end the scanning state. Immediately thereafter, the IMD application 824 conveys a new scan start request 1004C, and in response thereto, the RF circuit begins a new scanning state and opens a corresponding scanning window 1010C. The foregoing process continues until the scan reset pattern 1002 terminates or an advertisement notice is detected. Optionally, a desired delay may be introduced between the scan start requests and scan end requests.

The scan reset pattern 1002 iteratively restarts the scanning state, thereby directing a new scanning window 1010A-E to be started based on a scanning interval 1020A-D that substantially corresponds to the predetermined reset interval 1008A-D. In the embodiment of FIG. 10, the IMD application 824 directs the processor 804 to send scan start and scan end requests separated b a relatively short reset interval 1008A-D, such that only a single scanning window 1010A-E occurs within the reset intervals 1008A-D. Optionally, the reset intervals may space scan start and scan end requests further apart such that more than one scanning window occurs during any individual reset interval. Additionally or alternatively, the reset intervals may be set to differ in length such that a different number of scanning windows are opened between successive scan start and scan end requests.

Figure 11:
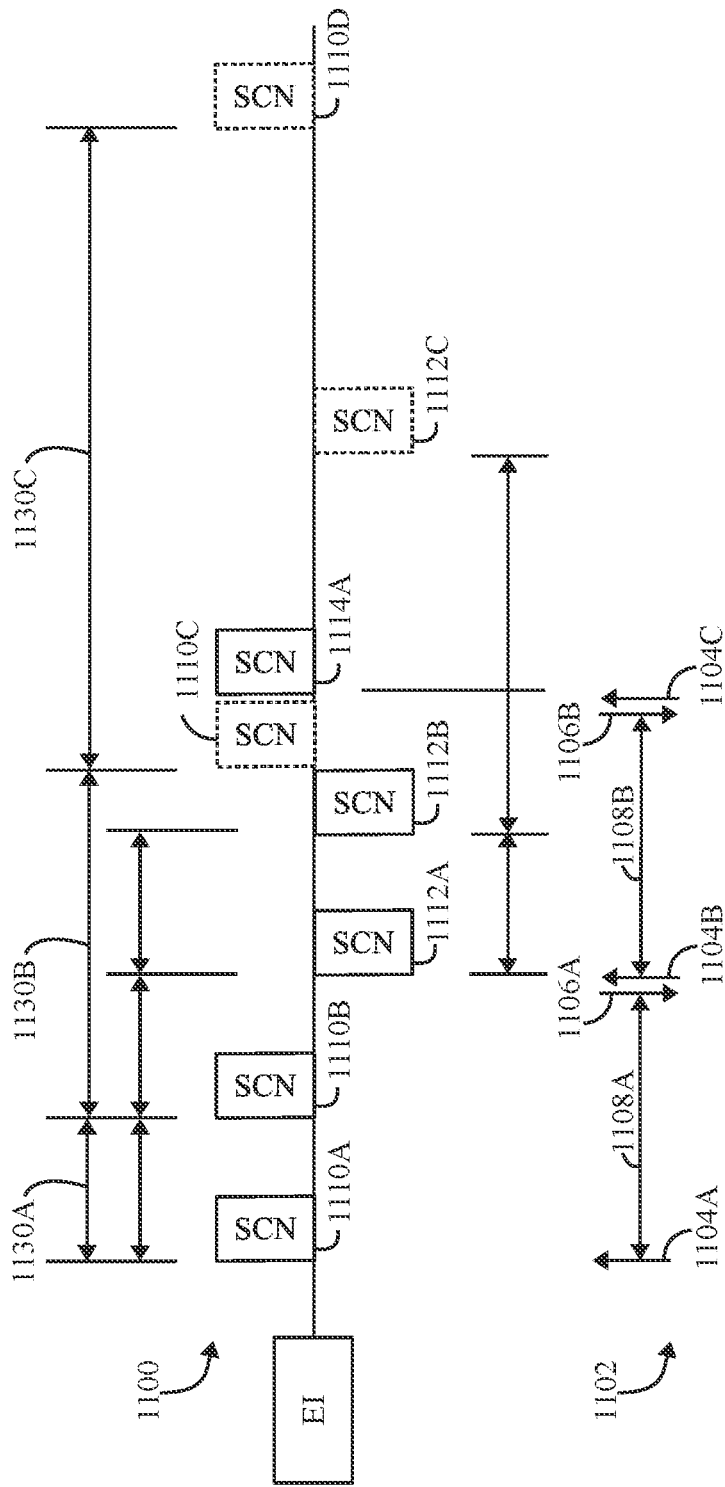
FIG. 11 illustrates a pseudo-scanning schedule utilized in accordance with embodiments herein.

FIG. 11 illustrates a pseudo-scanning schedule 1100 utilized in accordance with embodiments herein. The pseudo-scanning schedule 1100 is formed from a scan reset pattern 1102. The scan reset pattern 1102 is defined by a series of scan start requests 1104A-C and scan end requests 1106A-B which are designated by arrows directed upward and downward, respectively. The successive scan start and scan end requests 1004A-C, 1006A-B are separated by predetermined reset intervals 1108A-B.

FIG. 11 also illustrates the base scanning schedule that would be followed, but for the termination and restart of successive scanning states. The base scanning schedule includes scan intervals 1130A-C between actual and potential scanning windows 1110A-D. The actual scanning windows 1110A-B are utilized, while the potential scanning windows 1110 C-D are not utilized as the potential scanning windows are preempted by the scan reset pattern 1102. In response to a first scan start request 1104A, scanning windows 1110A-B are opened in accordance with the scanning interval 1130A. At the termination of reset interval 1108A, a scan end request 1106A is conveyed, followed shortly thereafter by a scan start request 1104B. The first scanning state is terminated by the scan end request 1106A, and thus the potential scanning window 1110C and 1110D are not opened. In response to the scan start request 1104B, a new/second scanning state is initiated and scanning windows 1112A-B are opened. If the second scanning state were continued, a potential scanning window 1112C would be utilized. However, before opening the potential scanning window 1112C, a scan end request 1106B is conveyed to the RF circuit and the potential scanning window 1112C is never used. Thereafter, a scan start request 1104C is conveyed to the RF circuit, to initiate a new/third scanning state, from which a scanning window 1114A is illustrated. The foregoing process is repeated until an advertisement notice is detected, the IMD application 824 "times out", or another predetermined criteria.

It is recognized that the examples of FIG. 10 and FIG. 11 are nonlimiting examples and that numerous other scan reset patterns may be utilized to define pseudo-scanning schedules.

The foregoing discussion has been in connection with IMDs operating in an advertising state, while external instruments operate in a scanning state. Optionally, the foregoing operations may be reversed, such that IMDs operate in a scanning state, while external devices operate in an advertising state. When the transmitting and scanning operations are reversed, the IMD implements the scanning operations in accordance with a corresponding scanning schedule as described herein. The external instrument implements advertising operations in accordance with a corresponding advertising schedule as described herein.

In accordance with embodiments herein, it is desirable to manage the IMD application running on the EI to connect with the IMD on a periodic basis (e.g., nightly). For example, the IMD application may direct the RF circuit of the EI to connect with the IMD through a wireless protocol (e.g., Bluetooth) at a scheduled connection time that is generally at a time of night where the patient is normally asleep (e.g., 1:00 AM, 3:00 AM, etc.) The IMD application performs the nightly connections in order to collect data, perform other maintenance tasks and the like. Typically, at the scheduled connection time, the OS and the IMD application are operating in a background state or mode. Thus, the IMD application initiates the connection request while the IMD application and/or the OS are running in the background state.

Figure 12:
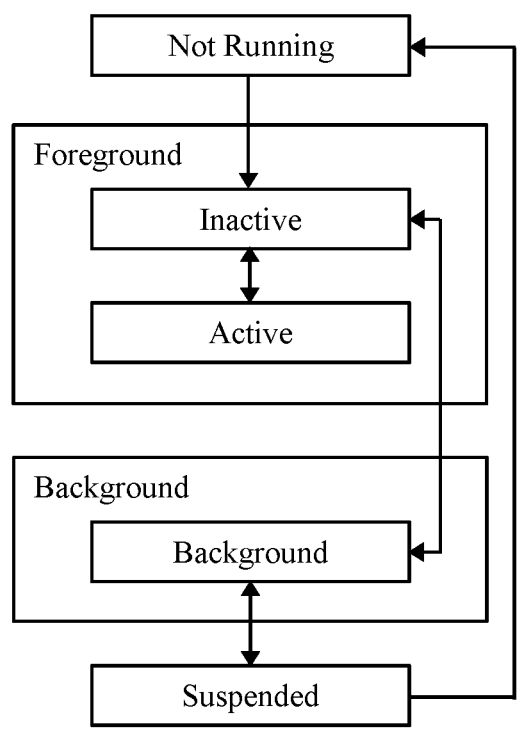
FIG. 12 illustrates a block diagram of the example in which an application may exist in accordance with embodiments herein.

The terms "mode" and "state" are used to refer to the execution or "run time" state of an application or operating system. For example, from the time that an application launches to the time the application quits, the application follows an execution path. During a life of an application, the application may transition between various states. FIG. 12 illustrates a block diagram of the example in which an application may exist. The states include "Not Running", "Inactive", "Active", "Background", "Suspended", and "Foreground". In the not running state, the application was terminated by the system and is not launched nor running. An application in a foreground state may also be in an active state or in active state. In the inactive state, the application is running in the foreground but is currently not receiving events (e.g., the application may be executing other code). An application may stay in the inactive state briefly as the application transitions to a different state. In the active state, the application runs in the foreground and receives events. The foreground state is the normal active mode for most applications. In the background state, the application is executing code in the background. When in the suspended state, the application is also in the background state, but is not executing code. An application may transition between states based on the internal functionality of the application, based on instructions from a user, based on instructions from the OS and otherwise.

In accordance with embodiments herein, the IMD application may launch in the foreground state or background state. When the IMD application launches in the foreground state, the IMD application may operate in the foreground state for some period of time and then move to the background state (e.g., when the OS transitions to the background state). The IMD application may continue to operate in the background state continuously or for an extended period of time.

When the IMD application transitions to a new state, the features and functionality of the IMD application may change. For example, the IMD application may be configured to perform a wide variety of IMD related features and functionality when operating in a foreground state. However, the IMD application may be configured to perform very limited IMD related features and functionality when operating in the background state.

In accordance with embodiments herein, methods and systems improve wireless connectivity between the IMD and the EI regardless of whether the OS and/or IMD application are operating in the foreground state or the background state. When an EI sends a connect request through the RF circuit to the IMD, the connection request may not time out. However, over time the RF circuit will slow down the scan rate. As noted herein, the IMD may advertise at a relatively slow rate (e.g., 4 pulses in 4 minutes). Hence, a connection success rate at the first advertising pulse slows down as the RF circuit slows the scan rate.

In accordance with embodiments herein, the IMD application manages communications operations (e.g., Bluetooth operations) differently when in the foreground state or background state. The IMD application modifies the base scan schedule utilized by the RF circuit to provide a better success rate for connecting with an IMD that transmits advertisement notices at a slow rate in accordance with a desired protocol (e.g., a BLE peripheral). Embodiments herein handle connect requests from the IMD application regardless of whether in foreground or background states. The IMD application manages the scanning window in accordance with one or more of the pseudo-scanning schedules discussed herein or in accordance with the base scanning schedule based on the whether the IMD application is running in a foreground state or a background state.

A technical effect of embodiments herein is to manage use of the pseudo-scanning and base scanning schedules, such that the IMD application is able to connect with the IMD utilizing the first advertising pulse with a desired success rate (e.g., more than 95% success rate), regardless of whether in the background or foreground state. A technical effect of embodiments herein is to account for scenarios in which the connect request is initially sent while in a foreground state, and then the OS and/or IMD application is moved to the background state. Another technical effect of embodiments herein is to account for scenarios in which the connect request is sent while in the background state and then the OS and/or IMD application move to the foreground state. a technical effect of embodiments herein is to avoid canceling a connection that may have been established shortly after expiration of the scan timer.

Figure 13:
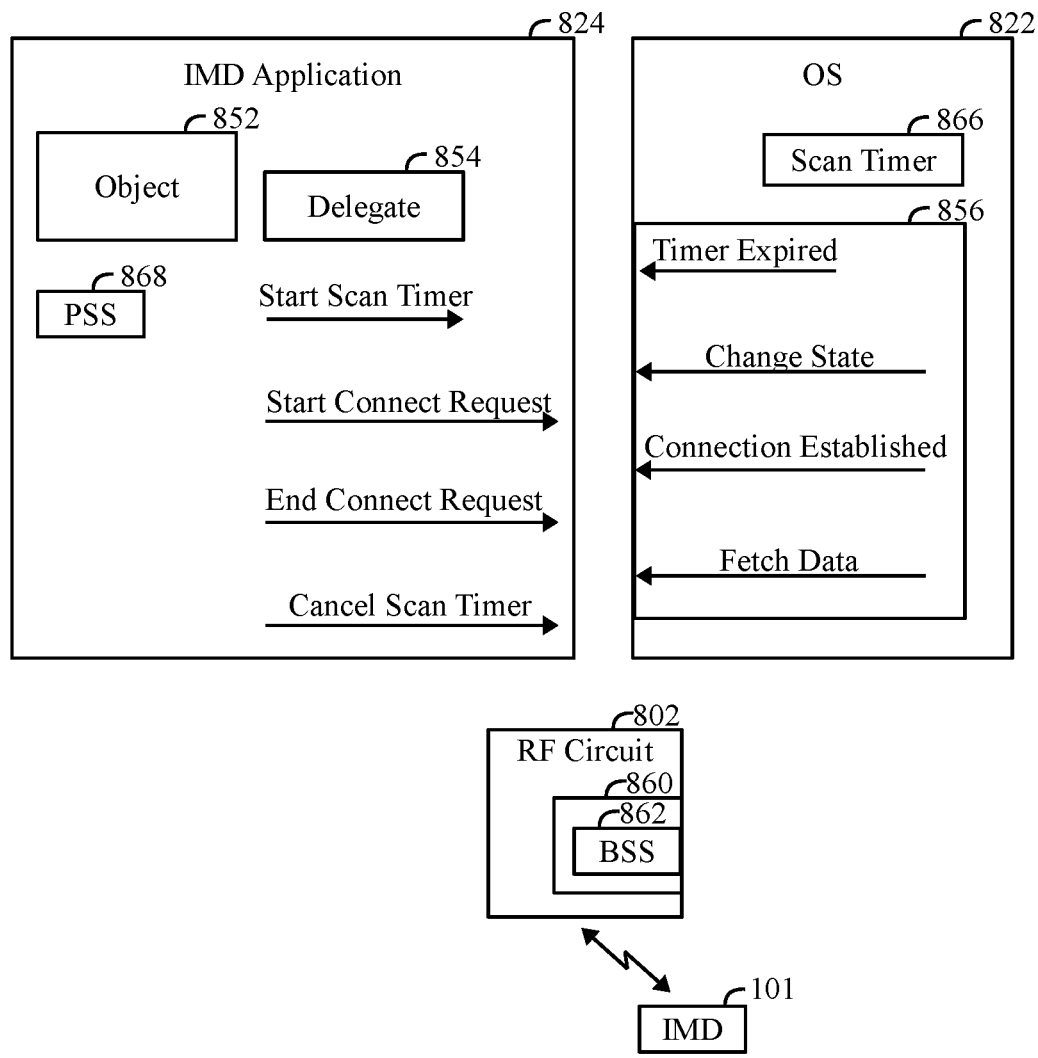
FIG. 13 illustrates a functional diagram of the interaction between the IMD application, OS and RF circuit in accordance with embodiments herein.

FIG. 13 illustrates a functional diagram of the interaction between the IMD application, OS and RF circuit in accordance with embodiments herein. The RF circuit 802 includes memory 860 that stores a base scanning schedule (BSS) 862 that defines a pattern for scanning windows over a scanning state. The base scanning schedule 862 may be defined within the firmware or software of the OS 822, the RF circuit 802 or otherwise in accordance with embodiments herein. For example, the BSS 862 may represent a predefined schedule as defined by the BLE protocol and the like. The OS 822 includes a scan timer 866 that is set based on a scan reset pattern to form a pseudo-scanning schedule 868 that differs from the base scanning schedule 862. The scan reset pattern defines a pattern for scan start requests and scan end requests that are separated by a predetermined reset interval to form the pseudo-scanning schedule 868. For example, the IMD application 824 may inform the OS 822 of the duration of the scan timer 866, as well as when to start and stop the scan timer 866.

The IMD application 824 includes one or more objects 852 that implement various features and functionalities in connection with the IMD, including but not limited to communication with the IMD 101. For example, the objects 852 may collect physiologic, device-related and other types of data and information from the IMD 101 and forward such information to a remote network or server. The objects 852 may manage the display of the IMD related data and information on the user interface of the EI, as well as allow the user of the EI (e.g. patient) to perform limited interaction with the IMD.

The IMD application 824 includes one or more delegate 854 that performs various operations. The delegate 854 represents one example of a manner by which commands, request, data, information and the like, are transferred between the IMD application 824 and other hardware and software modules within the EI. For example, a delegate 854 may respond to changes in state of the IMD application 824 (e.g. transitions between foreground and background states). The delegate 854 may send outgoing notifications and events, such as commands, request, data, information and the like, from the IMD application. For example, an outgoing notification may direct the OS 822 to start or cancel a scan timer 866 related to a reset scan pattern. An outgoing notification may represent a start connection request or end connection request conveyed to the OS 822 and/or the RF circuit 802. An outgoing notification may represent an end scan request or a start scan request conveyed to the OS 822 and/or RF circuit 802.

The delegate 854 may respond to incoming notifications, such as notifications from the OS 822, from the RF circuit 802 and the like. The delegate 854 may respond to events directed to the IMD application 824. By way of example, an incoming notification may indicate that a connection was established, a scan timer has expired, the application should transition to a new state (e.g. from the foreground to the background, from the background to the foreground, etc.). Optionally, an incoming notification may indicate that a connection request has been canceled, a scan timer has been started and the like. Optionally, an incoming notification may inform the IMD application 824 that data is present for download (e.g. data incoming from the IMD), inform the IMD application 824 that events related to a URL session are waiting to be processed (e.g. incoming or outgoing communications with a remote server or network). The incoming notifications may be maintained within a notification queue 856 until individual notifications are processed by the IMD application 824. The notification queue 856 may be maintained at the OS 822, at the delegate 854, within the RF circuit 802, and/or at another memory location. The notifications are processed by the delegate 854 in the order received, namely a first-in first-out order. It is recognized that the notification queue 856 may not include some or all of the example notifications illustrated in FIG. 13.

The IMD application 824 may also include a pseudo-scanning schedule 868, such as described herein in connection with various embodiments (e.g. FIGS. 10-11). Optionally, the pseudo-scanning schedule 868 may be stored elsewhere in memory and/or in firmware.

Figure 14:
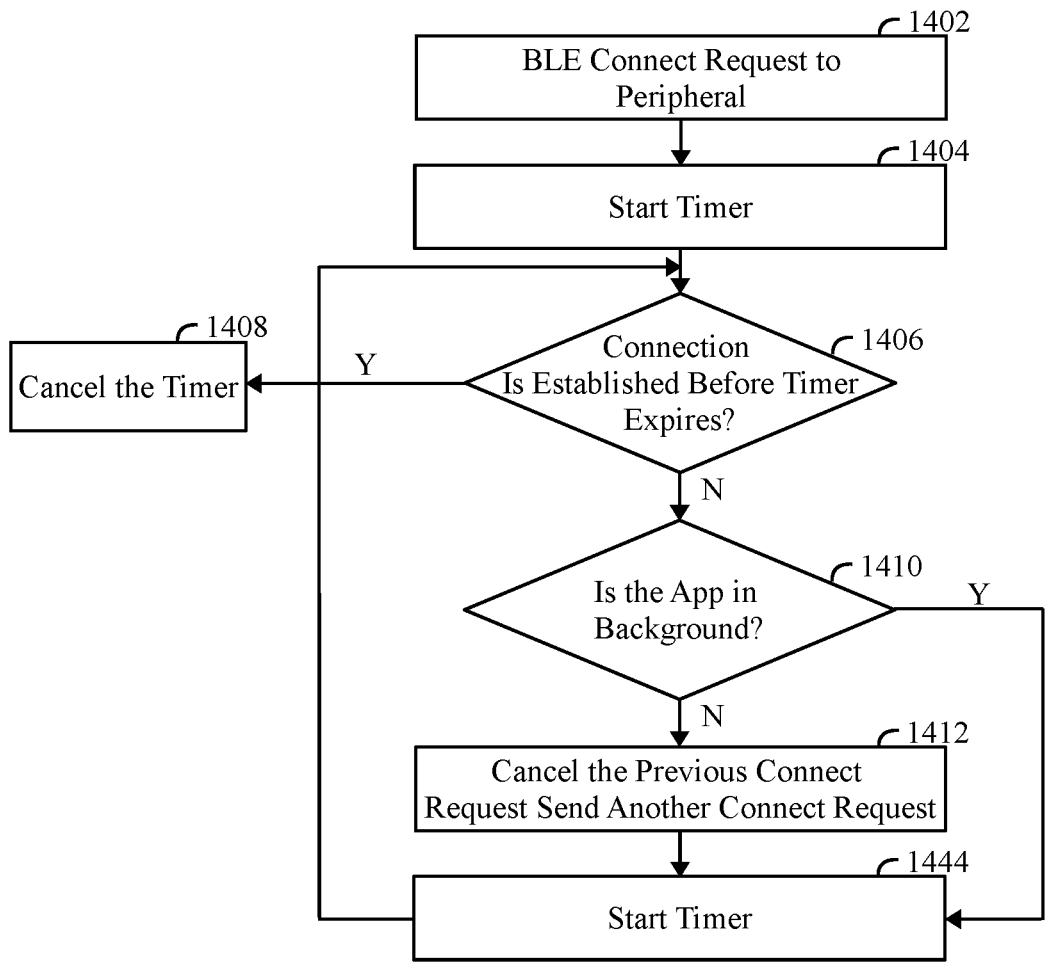
FIG. 14 illustrates a method for managing the scanning schedule, based on the operating state, in accordance with embodiments herein.

FIG. 14 illustrates a method for managing the scanning schedule, based on the operating state, in accordance with embodiments herein. At 1402, one or more processors, under the direction of the IMD application 824, direct the transceiver of the RF circuit 802 to transmit a connection request to the IMD 101. For example, a start connection request notification may be conveyed by the delegate 854 to the OS 822 and/or RF circuit 802. In response to the start connection request notification from the IMD application 824, the RF circuit 802 enters a scanning state during which a transceiver of the RF circuit 802 scans for an advertisement notice during scanning windows. By way of example, the connect request may be a BLE connection request sent by the IMD application 824.

At 1404, the one or more processors, under the direction of the IMD application 824, start a scan timer. For example, the delegate 854 conveys a start scan timer notification to the OS 822. In response thereto, the OS 822 starts a scan timer 866 that runs while the OS 822 is in the foreground or background state. The scan timer 866 may represent a software timer that is started with a timeout value that is set by the IMD application 824 based on the pseudo-scanning schedule 868. The timeout value may be configurable (e.g.

five seconds) and may be programmed at the time the IMD application 824 is installed or thereafter, such as over an Internet connection.

At 1406, the one or more processors, under the direction of the IMD application 824, determine whether a connection has been established with the IMD before the scan timer 866 expires. For example, the object 852 and delegate 854 determine whether a connection established notification has been received from the queue notification 856, and that no timer expired notification has been received from the queue notification 856. When a connection is established before the timer expires, flow moves to 1408.

At 1408, the one or more processors, under the direction of the IMD application 824, cancel the scan timer 866. For example, the delegate 854 conveys a cancel scan timer notification to the OS 822. At 1406, when a connection has not yet been established, but the scan timer expires, flow moves to 1410. At 1410, the one or more processors, under the direction of the IMD application 824, determine whether the OS 822 and/or IMD application 824 are running in the foreground state or background state. When the OS 822 and/or IMD application 824 are running a background state, flow moves to 1414. When the OS 822 and/or IMD application 824 are running in a foreground state, flow moves to 1412. At 1412, the one or more processors, under the direction of the IMD application 824, terminate/cancel a previous connection request and direct the transceiver to begin transmission of a new connection request. For example, the delegate 854 conveys an end connection request notification followed by a start connection request notification to the OS 822 and/or RF circuit 802. At 1414, the one or more processors, under the direction of the IMD application 824, start a new timer and flow returns to 1406. For example, the delegate 854 conveys a start scan timer notification to the OS 822. Thereafter, flow returns to 1406.

The operations at 1406-1414 are iteratively repeated to manage the scanning window in accordance with the pseudo-scanning schedule 868 or the base scanning schedule 862 dependent upon whether the OS 822 and/or IMD application 824 is running in the foreground state or background state. When in the foreground state, the managing operation manages the scanning window in accordance with the pseudo-scanning schedule 868. When in the background state, the managing operation manages the scanning window in accordance with the base scanning schedule 862. The IMD application 824 identifies that the scan timer 866 expires before an advertising notice is detected during one of the scanning windows. In response to the identifying operation, when in the background state, the IMD application 824 automatically restarts the scan timer 866 and continues the scanning state according to the base scanning schedule 862. For example, the base scanning schedule 862 may correspond to a Bluetooth connection schedule, where the pseudo-scanning schedule 868 has a higher duty cycle than a duty cycle corresponding to the Bluetooth connection schedule. The IMD application 824 identifies that the scan timer 866 expires before the advertising notice is detected during one of the scanning windows. In response to the identifying operation, when in the foreground state, the IMD application 824 automatically restarts the scan timer 866, cancels the scanning state and enters a new scanning state defined by the base scanning schedule. The cancelling and entering operations comprise cancelling a first connection request to the RF circuit 802 and sending a second connection request to the RF circuit 802.

If the scan timer 866 expires before establishing the BLE connection (at 1406) and if the IMD application 824 is in the foreground state (at 1410), then the previous connect request is cancelled, a new connect request is sent (at 1412) and another scan timer is started (1414). Alternatively, if the scan timer 866 expires (at 1406) and the IMD application 824 is in the background state (at 1410), then the IMD application 824 does not send a new connect request and the scan timer 866 is simply started again (1414). If the scan timer 866 expires while in the background state (1410), a new connection request is not sent because a connection may have been established after the scan timer 866 expired. The process of FIG. 14 acts upon the incoming notifications in the notification queue 856 on a first-in first-out basis. Accordingly, a timer expired notification may be loaded into the queue 856 before a connection established notification or a change to foreground state notification. At the time that the process of FIG. 14 acts upon a timer expired notification, the IMD application 824 does not yet know whether the notification queue 856 also includes a connection established notification or a change to foreground state notification. Accordingly, when it is determined (at 1406) that the scan timer 866 has expired and (at 1410) that the IMD application 824 is still in the background state, the outstanding connection request is not canceled.

By starting a new timer at 1414, the IMD application 824 then steps through the next iteration at 1406 to process the next notification within the notification queue 856. For example, the next notification, following the timer expired notification may be a change to foreground state notification. Accordingly, at 1410, a determination is made that the IMD application 824 is in the foreground state and thus flow moves to 1412 where the previous connection request is canceled. Additionally or alternatively, during a subsequent iteration, at 1406, the IMD application 824 processes a connection established notification and flow moves to 1408. In the foregoing manner, embodiments herein avoid canceling a connection that may have been established shortly after expiration of the scan timer.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for managing communications between an external instrument (EI) and an implantable medical device (IMD) in accordance with a communications protocol having a base scanning schedule that defines scanning windows over a scanning state, the method comprising:
    entering the scanning state, for at least one of the IMD or the EI, during which a receiver scans for advertisement notices during the scanning windows;
    automatically restarting the scanning state to form a pseudo-scanning schedule that differs from the base scanning schedule; and
    establishing a communication session between the IMD and the EI, wherein the base scanning schedule corresponds to a Bluetooth connection schedule, and wherein the scan reset pattern causes the pseudo-scanning schedule to have a higher duty cycle than a duty cycle corresponding to the Bluetooth connection schedule.

2. The method of claim 1, wherein the scanning state is restarted based on a scan reset pattern.

3. The method of claim 2, wherein a portion of the scanning windows occur in a first segment of the scanning state based on a first duty cycle and a remainder of the scanning windows occur in a second segment of the scanning state based on a second duty cycle that is lower than the first duty cycle.

4. The method of claim 3, wherein the scan reset pattern defines the pseudo-scanning schedule to have a pseudo-duty cycle that is higher than at least the second duty cycle associated with the second segment.

5. The method of claim 1, wherein the scanning windows in a second segment of the scanning state are spaced apart based on a second scanning interval that is longer than a scanning interval between the scanning windows in a first segment of the scanning state.

6. The method of claim 5, wherein the scan reset pattern defines the pseudo-scanning schedule to have a scanning interval between the successive scanning windows that is shorter than the second scanning interval associated with the second segment.

7. The method of claim 1, wherein an EI stores an application in memory, the application configured to communicate with the IMD, the application automatically restarting the scanning state to form the pseudo-scanning schedule.

8. The method of claim 7, wherein the base scanning schedule, scan reset pattern and the pseudo-scanning schedule are asynchronous with respect to advertising operations by the IMD.

9. The method of claim 1, further comprising:
determining whether an IMD communications application is running in a foreground state or a background state;
when in the foreground state, managing the scanning window in accordance with the pseudo-scanning schedule; and
when in the background state, managing the scanning window in accordance with the base scanning schedule.

10. A device, comprising:
a radio frequency (RF) circuit configured to communicate with a second device in accordance with a communications protocol having a base scanning schedule that defines a pattern for scanning windows over a scanning state, the RF circuit configured to enter the scanning state to scan for advertisement notices;
memory configured to store program instructions;
a processor that, when executing the program instructions, is configured to:
direct the RF circuit to automatically restart the scanning state based on a pseudo-scanning schedule that differs from the base scanning schedule, the base scanning schedule and the pseudo-scanning schedule being asynchronous with respect to advertising operations by the second device; and
establish a communication session with the second device.

11. The device of claim 10, wherein a portion of the scanning windows occur in a first segment of the scanning state based on a first duty cycle and a remainder of the scanning windows occur in a second segment of the scanning state based on a second duty cycle that is lower than the first duty cycle.

12. The device of claim 10, wherein the processor is configured to restart the scanning state based on a scan reset pattern that is asynchronous with respect to a distribution of the advertising notices.

13. The device of claim 12, wherein the scan reset pattern includes a predetermined reset interval, the processor configured to direct the RF circuit to end the scanning state before the end of the base scanning schedule and start a new scanning state at the expiration of the predetermined reset interval asynchronous with respect to advertising operations.

14. The device of claim 10, wherein the processor is configured to repeatedly end and restart successive new scanning states before the end of the base scanning schedule until the RF circuit detects an advertisement notice during one of the scanning windows.

15. The device of claim 11, wherein the scan reset pattern defines the pseudo-scanning schedule to have a pseudo-duty cycle that is higher than a duty cycle associated with the second segment.

16. The device of claim 10, wherein the scanning windows in a second segment of the scanning state are spaced apart based on a second scanning interval that is longer than a scanning interval between the scanning windows in a first segment of the scanning state.

17. The device of claim 10, wherein the device is further configured to determine:
whether a communications application is running in a foreground state or a background state;
when in the foreground state, manage the scanning window in accordance with the pseudo-scanning schedule; and
when in the background state, manage the scanning window in accordance with the base scanning schedule.

18. The device of claim 10, wherein the device represents an external instrument (EI) configured to communicate with an implantable medical device (IMD), the IMD representing the second device.

19. The device of claim 10, wherein the device represents an implantable medical device (IMD) configured to communicate with an external instrument (EI), the EI representing the second device.

* * * * *